(12) United States Patent
Knochenmuss

(10) Patent No.: US 9,366,650 B2
(45) Date of Patent: Jun. 14, 2016

(54) METHOD AND APPARATUS FOR DETERMINING A MOBILITY OF IONS

(75) Inventor: Richard Knochenmuss, Seftigen (CH)

(73) Assignee: TOFWERK AG, Thun (CH)

( * ) Notice: Subject to any disclaimer, the term of this patent is extended or adjusted under 35 U.S.C. 154(b) by 233 days.

(21) Appl. No.: 14/351,655

(22) PCT Filed: Aug. 13, 2012

(86) PCT No.: PCT/CH2012/000185
§ 371 (c)(1),
(2), (4) Date: Jun. 12, 2014

(87) PCT Pub. No.: WO2013/059947
PCT Pub. Date: May 2, 2013

(65) Prior Publication Data
US 2014/0326869 A1    Nov. 6, 2014

(30) Foreign Application Priority Data

Oct. 26, 2011   (EP) ..................................... 11405348

(51) Int. Cl.
*H01J 49/00*       (2006.01)
*G01N 27/62*       (2006.01)
(Continued)

(52) U.S. Cl.
CPC .............. *G01N 27/622* (2013.01); *H01J 49/02* (2013.01); *H01J 49/40* (2013.01)

(58) Field of Classification Search
CPC ... H01J 49/00; H01J 49/0027; H01J 49/0031; H01J 49/0036; H01J 49/02; H01J 49/022; H01J 49/025; H01J 49/06; H01J 49/061; H01J 49/062; H01J 49/067; H01J 49/22
USPC .......................... 250/281, 282, 293, 299, 287
See application file for complete search history.

(56) References Cited

U.S. PATENT DOCUMENTS 4,707,602 A * 11/1987 Knorr .................. G01N 27/622
                                                      250/281
6,781,120 B2    8/2004 LeCursi et al.
(Continued)

FOREIGN PATENT DOCUMENTS

CN       101562114     10/2009
WO       2004097394    11/2004

OTHER PUBLICATIONS

Guang Gong et al.: "Cryptographic Properties of the Welch-Gong Transformation Sequence Generators", IEEE Transactions on Information Theory, IEEE Press, USA, vol. 48, No. 11, Nov. 1, 2002, XP011074611, ISSN: 0018-9448.
(Continued)

*Primary Examiner* — Michael Logie
*Assistant Examiner* — Jason McCormack
(74) *Attorney, Agent, or Firm* — Jacox, Meckstroth & Jenkins

(57) ABSTRACT

A method and an apparatus for determining a mobility of ions. The method includes the steps of modulating an ion beam with an ion gate which is controlled by a modulation function for generating a modulated ion beam, of guiding the modulated ion beam through a drifting region, of measuring a signal of the modulated ion beam after the modulated ion beam has passed the drifting region and of calculating a correlation of the modulation function and the signal in order to determine the mobility of the ions. The apparatus includes the ion gate, the drifting region through which the modulated ion beam is guidable, a detector by which the signal of the modulated ion beam is measurable after the modulated ion beam has passed the drifting region and a calculation unit by which the correlation of the modulation function and the signal is calculable in order to determine the mobility of the ions. An autocorrelation of the modulation function is a two-valued function.

16 Claims, 13 Drawing Sheets

(51) Int. Cl.
*H01J 49/02* (2006.01)
*H01J 49/40* (2006.01)

(56) References Cited

U.S. PATENT DOCUMENTS

| | | |
|---|---|---|
| 6,782,342 B2 | 8/2004 | LeGore et al. |
| 6,900,431 B2 | 5/2005 | Belov et al. |
| 7,031,877 B2 | 4/2006 | LeGore et al. |
| 7,120,998 B2 | 10/2006 | LeCursi et al. |
| 7,403,867 B2 | 7/2008 | LeGore et al. |
| 7,417,222 B1 * | 8/2008 | Pfeifer ............... H01J 49/0027 250/282 |
| 7,541,576 B2 | 6/2009 | Belov et al. |
| 8,022,359 B2 | 9/2011 | Michelmann |
| 2003/0048059 A1 | 3/2003 | LeCursi et al. |
| 2003/0055573 A1 | 3/2003 | LeGore et al. |
| 2004/0183007 A1 * | 9/2004 | Belov ............... H01J 49/401 250/287 |
| 2005/0086026 A1 | 4/2005 | LeGore et al. |
| 2005/0102829 A1 | 5/2005 | LeCursi et al. |
| 2006/0178844 A1 * | 8/2006 | LeGore ............... G01N 23/05 702/29 |
| 2006/0273253 A1 * | 12/2006 | Fitzgerald ............... H01J 49/04 250/287 |
| 2008/0173807 A1 * | 7/2008 | Yoon ............... H01J 49/0045 250/282 |
| 2008/0185513 A1 | 8/2008 | Belov et al. |
| 2009/0294647 A1 | 12/2009 | Michelmann |

OTHER PUBLICATIONS

Nam Yul Yu et al: "Crosscorrelation Properties of Binary Sequences with Ideal Two-Level Autocorrelation", Jan. 1, 2006, Sequences and Their Applications—SETA 2006 Lecture Notes in Computer Science;; LNCS, Springer, Berlin, DE, pp. 104-118, XP019043195, ISBN: 978-3-540-44523-4.

* cited by examiner

METHOD AND APPARATUS FOR DETERMINING A MOBILITY OF IONS

CROSS-REFERENCE TO RELATED APPLICATIONS

This application claims priority to European Application No. 11405348.1 filed Oct. 26, 2011 and to PCT Application No. PCT/CH2012/000185 filed Aug. 13, 2012, all of which are incorporated herein by reference and made a part hereof.

BACKGROUND OF THE INVENTION

1. Field of the Invention

The invention relates to a method and an apparatus for determining a mobility of ions. The method includes the steps of modulating an ion beam with an ion gate which is controlled by a modulation function for generating a modulated ion beam, of guiding the modulated ion beam through a drifting region, of measuring a signal of the modulated ion beam after the modulated ion beam has passed the drifting region and of calculating a correlation of the modulation function and the signal in order to determine the mobility of the ions. The apparatus includes the ion gate, the drifting region through which the modulated ion beam is guidable, a detector by which the signal of the modulated ion beam is measurable after the modulated ion beam has passed the drifting region and a calculation unit by which the correlation of the modulation function and the signal is calculable in order to determine the mobility of the ions.

2. Description of the Related Art

Another ion mobility spectrometer and a corresponding method are disclosed in U.S. Pat. No. 7,417,222 B1 (Sandia Corp). There as well, the ion beam is modulated with a modulation function and the measured signal is correlated with the modulation function. But in contrast to U.S. Pat. No. 2009/0294647 A1, the modulation function may also be a binary function. In particular, Barker codes are described as being favorable modulation functions because their autocorrelation provides low side bands.

Another ion mobility spectrometer and a corresponding method are disclosed in U.S. Pat. No. 7,417,222 B1 (Sandia Corp). There as well, the ion beam is modulated with a modulation function and the measured signal is correlated with the modulation function. But in contrast to U.S. Pat. No. 2009/0294647 A1, the modulation function may also be a binary function. In particular, Barker codes are described as being favourable modulation functions because their autocorrelation provides low side bands.

A somewhat different approach is described in U.S. Pat. No. 6,900,431 B1 (Predicant Biosciences, Inc.) on the example of a time of flight mass spectrometer. Here, the ion beam is modulated in pseudo random sequences of maximum length. The characterization of the ion spectra is obtained by the inverse Hadamard transformation formalism. Similarly, in the ion mobility spectrometer disclosed in WO 2004/097394 A1 (Smiths Group Plc), the ion beam is modulated with a pseudo random sequence of maximum length and the measured ion signal is analyzed by a matrix algebra. But in the latter example, a Fourier analysis may be used instead of the matrix algebra, too. Additionally, two modulation sequences with inverted bits may be used in order to obtain a better signal to noise ratio.

These known methods have in common that the ion beam is modulated according to a modulation function, that the ion signal is measured after the ions have passed a drifting region and that the ion mobility is obtained by calculating a correlation of the modulation function with the measured ion signal. This procedure for obtaining the ion mobility is employed because it is not required to know the starting time of each individual ion as it would be if directly measuring the ion's flight time. Consequently, it is possible to pass at the same time more than one pulse or packet of ions through the drifting region. This has the advantage that more ions can be measured within the same period of time.

The disadvantage of this procedure is that calculating the correlation introduces features into the ion mobility spectra which cannot easily be identified as such. For example, these features may be small peaks in the ion mobility spectra that look like a signal obtained from some specific ion species. Therefore, if traces of ions are to be detected, such artificially introduced features are likely to lead to misinterpretations of the ion mobility spectra. Thus, in order to avoid such misinterpretations, small peaks in the ion mobility spectra have to be discarded as possible false peaks. This significantly limits the attainable dynamic range.

SUMMARY OF THE INVENTION

It is the object of the invention to create a method and an apparatus pertaining to the technical field initially mentioned that allow for determining an ion mobility with a higher signal to noise ratio while providing the same measurement speed as known from the prior art.

The solution of the invention is specified by the features of the independent claims. According to the invention, the autocorrelation of the modulation function is a two-valued function. This means that the autocorrelation function has a peak at zero and a constant value at all other points.

The advantage of the modulation function having a two-valued autocorrelation function is that calculating the correlation does not introduce additional features into the ion mobility spectra.

Preferably, the modulation function is a binary function. Accordingly, the modulation function may be represented by a row of bits. This has the advantage that it is simple to modulate with the ion gate the ion beam such that in flight direction of the ions the modulated ion beam has the shape of the modulation function. In a variant, the modulation function is based on a binary function but provides smoothed steps between the bits of the binary function. This has the advantage that depletion of ions in a region behind the ion gate and tailing or diffusion of ions in the modulated beam can be taken into account for by adapting the modulation function to these effects in the modulated ion beam before calculating the correlation. In a further variant, the modulation function is based on a binary function but is oversampled. That is, multiple measurements are made during each "0" and "1" of the binary function. Alternatively, the modulation function is a non-binary function, which may also be oversampled.

In the following, there are passages where the modulation function is described as being a binary function or a sequence. In these passages, the modulation function may effectively be the described binary function or sequence. But it may as well be a function which is based on the described binary function or sequence. In the latter case, the modulation function may provide smoothed steps between the bits of the described binary function or sequence and/or may be oversampled.

Preferably, the modulation function is a pseudorandom sequence. This has the advantage that the properties of the modulation function approximate the properties of a random sequence. Therefore, repetitions in the modulation function that would lead to additional peaks in the ion mobility spectra can be avoided if the length of the pseudorandom sequence is chosen accordingly. Furthermore, a pseudorandom sequence as a modulation function has the advantage that the modulation function can easily be generated like for example with a linear feedback shift register.

If the modulation function is a pseudorandom sequence of the type known as maximum length sequences or of a type that can be represented by one ore more maximum length sequences, it is advantageous to use a linear feedback shift register for generating the modulation function. In such a linear feedback shift register a number of feedback patterns are possible, called tap sets of the linear feedback shift register. The number of possible tap sets depends on the length of the particular linear feedback shift register. The modulation function is generated with the linear feedback shift register by choosing a tap set and a set of initial values. The set of initial values is fed to the linear feedback shift register. Based on the set of initial values, the modulation function is then generated by the linear feedback shift register according to the tap set. Therefore, the modulation function depends on the tap set and on the set of initial values.

As a variant, the modulation function may be generated in a different way. For example, one or more known pseudorandom sequences or other modulation functions may be stored in a data store. For each measurement, a particular modulation function stored in the data store may be used.

In a further variant, the modulation function may be a different function than a pseudorandom sequence. For example, it may be a random sequence. This has the advantage that the function has the corresponding properties. Alternatively, the modulation function may be a non-random function.

If the modulation function is a pseudorandom sequence, it is advantageously a maximum length sequence, a GMW sequence, a Welch-Gong transformation sequence, a Quadratic residue sequence, a Sextic residue sequence, a Twin prime sequence, a Kasami power function sequence, a Hyperoval sequence or a sequence derived from 3 or 5 maximum length sequences. This has the advantage that the modulation function is a sequence with well known properties. In case the sequence is derived from 3 to 5 maximum length sequences, it may for example be obtained by adding up the content of corresponding bits of the 3 or 5 maximum length sequences. In that case, the addition of two 1s or of two 0s may result in a 0, while the addition of a 0 and a 1 or of a 1 and a 0 may result in a 1 (bitwise NAND operation).

As a variant, the modulation function may be a pseudorandom sequence which does not belong to one of these classes.

Preferably, if the modulation function is a binary function or a sequence, it has a length of more than 15 bits, preferably more than 50 bits, in particular more than 100 bits. This has the advantage that the modulation function is long enough to enable measurements where sufficient ions are being measured for obtaining meaningful ion mobility spectra.

Alternatively, the modulation function may have a length of 15 bits or less. This may be advantageous if the time of a measurement should be short and if there are sufficient ions available for obtaining meaningful ion mobility spectra.

Advantageously, the method comprises a step of enhancing the edges of the signal with a filter by filtering the signal before calculating the correlation. This has the advantage that the resolution of the obtained ion mobility spectra is improved in that the correlation is sharpened.

Alternatively, the method may not comprise a step of enhancing the edges of the signal with a filter before calculating the correlation. If the obtained ion mobility spectra should be as close as possible to the effectively measured signal, leaving out the step of enhancing the edges of the signal may be advantageous because the required filtering is a treatment of the measured signal.

If the method comprises the step of enhancing the edges of the signal with a filter, the filter is preferably an n-element finite difference filter, an edge enhancement filter or a filter using a different type of sharpening algorithm. This has the advantage that an enhancing of the edges of the signal is obtained with a known sharpening algorithm which can be adjusted to the particular characteristics of the signal to be treated.

For example, in case the filter is an n-element finite difference filter and the signal is measured in bins having a specific width in time, the filter may comprise an algorithm having the form $$F_i = 2nD_i - \sum_{j=i+1}^{i+n} D_j - \sum_{j=i-n}^{i-1} D_j,$$

where n is a measure for the width of the filter, $D_i$ is the size of the signal's $i^{th}$ bin and $F_i$ is the filter-value's $i^{th}$ bin. In order to obtain the filtered signal, each filter-value $F_i$ is added to the corresponding bin $D_i$ of the measured signal. When doing so, it is possible to multiply the filter-values $F_i$ and/or the signal $D_i$ with a weight factor before adding the filter-values to the signal. For example, such a weight factor may be based on n, the width of the filter, with $0 <= n <= n_{max}$:

$$D_i^{Filtered} = \frac{1-n}{n_{max}} D_i + \frac{n}{n_{max}} F_i.$$

Of course, it is possible to use weight factors that are independent of the width of the filter as well. Furthermore, it is possible to flatten the signal $D_i$ before calculating the filter-value by convoluting the signal with a Gaussian or any other smoothing function. This may be advantageous because otherwise, noise in the signal may lead to errors in the filter-value.

If the signal is not measured in bins having a specific width in time but by storing for each measured ion (i.e. for each event) the time passed since a starting time, the signal may be rasterized to bins of a specific width in time before applying the filter. Alternatively, if for each event the time is stored which has passed since the starting time, the filter's algorithm may be adapted to take into account for the time differences between the individual events instead of assuming bins having a specific width in time. The parameter n of the algorithm may then become a measure for the time interval within which events are considered when calculating a particular filter-value $F_i$.

In case the signal is measured or rasterized in bins having a specific width in time, it is advantageous that n, the number of bins considered, is adapted to the characteristics of the signal. If the filter should be calculated rapidly, it may be advantageous to choose n to be 1. In this case, the filter becomes a Laplace filter. Otherwise, if the signal is neither measured in bins having a specific width in time nor rasterized accordingly, it is advantageous to adapt to the characteristics of the signal the time interval within which events are considered.

For example, in case the filter is an edge enhancement filter, it may comprise an algorithm where a blurred signal is calculated by convoluting the signal with a Gaussian, and where the difference between the signal and the blurred signal is added to the signal. Similar to the method of unsharp masking known from digital image processing, three parameters of the algorithm may be adapted according to the particular signal to be treated. First, the width of the Gaussian may be adapted. Second, before adding the difference to the signal, the difference may be multiplied by a weighting factor that is adapted to the particular signal. Third, a threshold parameter may be defined such that the filter is only applied if the parameter's value is above a certain threshold. For example, the threshold parameter may be the deviation of the blurred signal from the measured signal.

If the method does not comprise a step of enhancing the edges of the signal with a filter by filtering the signal before calculating the correlation, the method preferably comprises a step of calculating from the signal a blurred signal and a step of calculating a difference between the signal and the blurred signal by subtracting the blurred signal from the signal, before the correlation of the modulation function and the difference between the signal and the blurred signal is calculated. This has the advantage that the resolution of the obtained ion mobility spectra is improved in that the correlation is sharpened.

If the method comprises the two additional steps as explained above and if the signal is not measured in bins having a specific width in time but by storing for each measured ion (i.e. for each event) the time passed since a starting time, the signal may be rasterized to bins of a specific width in time before calculating the blurred signal. Alternatively, the signal and the blurred signal may be rasterized to bins of a specific width in time before calculating the difference between the signal and the blurred signal. Independent of whether the signal is measured in bins having a specific width in time or whether for each measured ion (i.e. for each event) the time passed since a starting time is measured and subsequently rasterized to bins, the width in time of the bins is advantageously smaller than the width in time of the bits of the modulation function. Preferably, the width in time of the bins is three to ten times smaller than the width in time of the modulation function's bits. Alternatively, the bin's width in time is more than ten times smaller than the width in time of the modulation function's bits.

Alternatively, the method may neither comprise a step of calculating from the signal a blurred signal nor comprise a step of calculating a difference between the signal and the blurred signal by subtracting the blurred signal from the signal. If the obtained ion mobility spectra should be as close as possible to the effectively measured signal, leaving out these two steps may be advantageous because they are a treatment of the measured signal.

If the method comprises a step of calculating from the signal a blurred signal and a step of calculating a difference between the signal and the blurred signal by subtracting the blurred signal from the signal, and if the signal is measured in bins having a specific width in time, the blurred signal is advantageously calculated by convoluting the signal with a function. Such a function may be for example a Gaussian, a Lorentzian or another symmetric function providing a single peak. Alternatively, the blurred signal may be calculated with a method which is different from calculating a convolution.

If the method comprises a step of calculating from the signal a blurred signal and a step of calculating a difference between the signal and the blurred signal by subtracting the blurred signal from the signal, and if for each measured ion (i.e. for each event) the time passed since a starting time is measured and subsequently rasterized to bins, the blurred signal is advantageously calculated by amending the measured time for each ion by a value determined from a probability distribution. For this probability distribution, a Gaussian distribution or a different, symmetric probability distribution with a single peak of highest probability may be chosen. After the calculating the blurred signal, the signal and the blurred signal are advantageously rasterized to bins of a specific width in time before calculating the difference between the signal and the blurred signal. In a preferred variant, if for each measured ion (i.e. for each event) the time passed since a starting time is measured, the signal is rasterized to bins of a specific width in time before calculating the blurred signal. In this latter case, the blurred signal is advantageously calculated by convoluting the signal with a function like for example a Gaussian, a Lorentzian or another symmetric function providing a single peak. But in a variant, the blurred signal may be calculated with a method which is different from calculating a convolution.

If the blurred signal is calculated by convoluting the signal with a function or by amending for each individual ion the time measured for this ion by a value determined from a probability distribution, the function or the probability distribution, respectively, is preferably chosen to have a half width at half maximum or a standard deviation which is smaller than half the width in time of a bit of the modulation function. Alternatively, the function or the probability distribution may be chosen such that the function or the probability distribution, respectively, has a half width at half maximum or a standard deviation which is half or more than the width in time of a bit of the modulation function.

If the method comprises a step of calculating from the signal a blurred signal and a step of calculating a difference between the signal and the blurred signal by subtracting the blurred signal from the signal, the signal and the blurred signal are advantageously weighted relative to each other for calculating the difference. In a preferred variant, the blurred signal is weighted to have an integral intensity of 100% of the integral intensity of the signal. In another preferred variant, the blurred signal is weighted to have an integral intensity of less than 100% of the integral intensity of the signal but of more than 90% of the integral intensity of the signal. In still another preferred variant, the blurred signal is weighted to have an integral intensity of less than 100% of the integral intensity of the signal but of more than 80% of the integral intensity of the signal. Alternatively, the blurred signal is weighted to have an integral intensity of less than 80% of the integral intensity of the signal.

If the method comprises a step of calculating from the signal a blurred signal and a step of calculating a difference between the signal and the blurred signal by subtracting the blurred signal from the signal, the method preferably comprises an additional step of setting negative values of the calculated correlation to a value of zero or an arbitrary positive value. This has the advantage that negative values in the correlation are omitted since they do not provide any information on the ion mobility spectrum.

Alternatively, the method does not comprise the step of setting negative values of the calculated correlation to a value of zero or an arbitrary positive value.

Advantageously, an interval of interest of possible ion drift times is chosen from the correlation. This has the advantage that the interval of interest of the ion mobility spectra may be displayed or used for further data treatment. Alternatively, no specific interval of interest of possible ion drift times is chosen from the correlation. This has the same effect as if the interval of interest is chosen to spread over the entire correlation. Accordingly, this alternative has the advantage that all data may be displayed or used for further data treatment, respectively.

If the correlation is calculated for an interval of interest of possible ion drift times, the method preferably comprises a step of selecting the modulation function such that as many as possible false peaks in the correlation are located outside of the interval of interest. These false peaks belong to a group of features in the ion mobility spectra that are already present in the measured signal in the form of imperfections and/or noise in the signal. The imperfections may be caused for example by depletion of ions in a region behind the ion gate, by tailing of ions in the modulated beam, by diffusion of ions in the modulated beam and/or by inhomogenities or turbulences in a gas flow in the drifting region. Such imperfections may lead to a change of the shape of the modulated ion beam. Accordingly, they may lead to unintended features in the measured signal. As a consequence of calculating the correlation, the feature's positions in the ion mobility spectra may be shifted as compared to their positions in the measured signal. The shifting behavior depends on the feature and on the modulation function. For example, if the modulation function is a sequence that is generated by a linear feedback shift register, the positions of some features in the ion mobility spectra are determined by the tap set of the linear feedback register while they are independent of the set of initial values used for generating the sequence. In the present context, the term "false peaks" is used for this particular group of features in the ion mobility spectra. Consequently, it is advantageous to use a linear feedback shift register for generating the modulation function and to use tap sets of the linear feedback shift register where the positions of false peaks caused by specific features are known. For example, tap sets may be preliminary evaluated for features which are characteristic for the ion mobility spectrometer that is used for executing the method. These characteristic features may be depletion of ions in a region behind the ion gate, tailing of ions in the modulated ion beam, diffusion of ions in the modulated ion beam and/or inhomogenities or turbulences in a gas flow in the drifting region. Once the interval of interest of possible ion drift times is known, the tap set which is used can be chosen such that the false peaks in the ion mobility spectra are located outside of the interval of interest. This has the advantage that the chances of a misinterpretation of the obtained ion mobility spectra are reduced.

Alternatively, it is possible to leave out the step of selecting the modulation function such that false peaks in the correlation are located outside of the interval of interest. This may be advantageous if the interval of interest is large and if the available modulation functions would be too strongly limited by such a selection or if there would be no corresponding modulation function available at all.

Preferably, the method comprises a step of selecting the modulation function such that false features in the correlation have a low height. Similar to the expression "false peaks", the expression "false features" is used in the present context for a particular group of features in the ion mobility spectra that are already present in the measured signal in the form of imperfections and/or noise in the signal. If the modulation function is a sequence that is generated by a linear feedback shift register, the position of a false feature in the ion mobility spectra depends on the tap set of the linear feedback shift register and on the set of initial values used for generating the sequence. In addition, the height of the false features depends on the set of initial values used for generating the sequence.

Accordingly, it is preferable to choose the modulation function such that characteristic imperfections like depletion of ions in a region behind the ion gate, tailing of ions in the modulated beam, diffusion of ions in the modulated beam and/or inhomogenities or turbulences in a gas flow in the drifting region result in a minimal height of the false features in the ion mobility spectra. This has the advantage that the chances of a misinterpretation of the obtained ion mobility spectra are reduced.

Alternatively, it is possible to leave out the step of selecting the modulation function such that false features in the correlation have a low height.

Preferably, the method comprises a step of determining a noise level of a correlation noise in a region of the calculated correlation where no signal of measured ions is expected and a step of calculating a noise-suppressed correlation by suppressing the correlation noise in the correlation, both steps being executed after the step of calculating the correlation. Hereby, the term "correlation noise" is used for noise which is included into the correlation when calculating the correlation of the modulation function and the signal because of statistical noise in the measured signal. Including these two steps into the method has the advantage that the signal to noise ratio in the correlation is improved. This advantage is obtained independent on whether the method comprises the step of enhancing the edges of the signal with a filter by filtering the signal before calculating the correlation or not. Furthermore, this advantage is obtained independent on whether the method comprises the steps of calculating from the signal a blurred signal and of calculating a difference between the signal and the blurred signal by subtracting the blurred signal from the signal or not. Nonetheless, the result is further improved if the method the step of enhancing the edges of the signal with a filter by filtering the signal before calculating the correlation or if the method comprises the steps of calculating from the signal a blurred signal and of calculating a difference between the signal and the blurred signal by subtracting the blurred signal from the signal.

Advantageously, the noise level of the correlation noise is determined in a region of the calculated correlation which corresponds to flight times that are shorter than the possible flight time of the fastest ions being measured. In a preferred variant, the noise level of the correlation noise is determined in a region of the calculated correlation which corresponds to flight times that are longer than the flight time of the slowest ions being measured. In the latter variant, the modulation function may be chosen to be longer in time than the flight time of the slowest possible or expected ions. This way, a region in the calculated correlation is obtained which represents flight times being longer than the slowest ions being measured and which can thus be used for determining the noise level. Alternatively, the noise level of the correlation noise may be determined in another region of the calculated correlation where no signal of measured ions is expected.

Preferably, a first value of the noise level of the correlation noise is calculated by calculating the average or median of the signal in the region of the calculated correlation where no signal of measured ions is expected. This has the advantage that the noise level provides a measure for the mean amplitude of the correlation noise. In a variant, the first value of the noise level of the correlation noise may be based on a minimal or maximal value of the signal in the region of the calculated correlation where no signal of measured ions is expected.

Independent on whether the first value of the noise level is determined by calculating an average or a median or by using a minimal or maximal value of the noise level, the first value of the noise level has the value of the average, median or minimal or maximal value of the noise level or is calculated by some formula from the value. In the latter case, the formula may be a simple multiplication with a scaling factor or may be a more complicated formula.

In a preferred variant, a second value of the noise level is calculated by calculating a standard deviation of the signal in the region of the calculated correlation where no signal of measured ions is expected. In a further preferred variant, the second value of the noise level of the correlation noise is determined by calculating by a Bayesian estimation process a remainder of the signal in the region of the calculated correlation where no signal of measured ions is expected. In a further variant, the second value of the noise level of the correlation noise is determined by a different method. For example, the second value of the noise level may be determined by calculating a difference between the first value of the noise level and a minimal value or a maximal value of the signal in the region of the calculated correlation where no signal of the measured ions is expected.

Independent on whether the second value of the noise level is determined by calculating a standard deviation, a remainder or any other measure, the second value of the noise level may be identical with the standard deviation, remainder or other measure or may be calculated by some formula from the standard deviation, remainder or other measure. In the latter case, the formula may be a simple multiplication with a scaling factor or may be a more complicated formula.

The calculation of a second value of the noise level has the advantage that the noise level provides a measure for the mean amplitude of the background signal as well as a measure for the amplitude of the scattering of the background signal. Both values can be used for calculating the noise-suppressed correlation.

Alternatively, the noise level may be a single value. In this case, the value of the noise level may be the above mentioned first value of the noise level, the above mentioned second value of the noise level, or may be the addition or difference of the first and second value of the noise level. In all three cases, the value can be used for calculating the noise-suppressed correlation.

If the method comprises a step of determining the noise level of the correlation noise in a region of the calculated correlation where no signal of measured ions is expected and a step of calculating a noise-suppressed correlation, the determined noise level is advantageously used for determining the amount the correlation noise is suppressed in the step of calculating the noise-suppressed correlation. This has the advantage that the amount of suppression of the correlation noise is adapted to the effective amount of correlation noise in the correlation. For example, one way to obtain the suppression is to test every value in the correlation on whether it is within the noise level or not. If the value is within the noise level, it may be reduced to a fixed amount, reduced by a fixed amount or reduced by a factor, while the value may be maintained if it is not within the noise level. In these examples, preferably the single value of the noise level or the first value of the noise level is used for calculating the noise-suppressed correlation. In another example, the suppression may be obtained by testing every value in the correlation on how likely it is correlation noise. Subsequently, the value may be reduced by an amount which is proportional to the likelihood of the value being correlation noise. In this latter example, preferably the first and the second value of the noise level are used for calculating the noise-suppressed correlation. This has the advantage that the first value of the noise level provides a measure for the mean noise level, while the second value of the noise level provides a measure for shape of the probability distribution for determining the likelihood of a particular value being correlation noise. Alternatively, the correlation noise may be suppressed with a different method.

If the method comprises a step of determining the noise level of the correlation noise in a region of the calculated correlation where no signal of measured ions is expected and a step of calculating the noise-suppressed correlation, the method comprises preferably a step of convoluting the noise-suppressed correlation with the modulation function for obtaining an estimated signal and of correlating the estimated signal with the modulation function for obtaining an estimated correlation, whereafter the steps of calculating the correlation of the modulation function and the estimated correlation, of determining the noise level of the correlation noise in a region of the resulting correlation where no signal of measured ions is expected and of calculating the noise-suppressed correlation are repeated. This has the advantage that due to the repetition, the correlation noise can be suppressed by a smaller amount per cycle such that true ion signals in the correlation are not affected, while the final correlation noise after the repetition is suppressed more strongly.

In a preferred variant, the steps of calculating the correlation of the modulation function and the estimated signal, of determining the noise level of the correlation noise in a region of the resulting correlation where no signal of measured ions is expected and of calculating the noise-suppressed correlation are repeated more than once. In this variant, the step of convoluting the noise-suppressed correlation with the modulation function for obtaining an estimated signal is repeated each time before the other steps are repeated. This has the advantage that in each repetition, the correlation noise can be suppressed by a smaller amount such that real signals in the correlation are not affected, while due to the repetition, the correlation noise is suppressed more strongly.

In a further preferred variant, these steps are repeated a fixed number of times like for example once, twice, three times, five times or ten times. This has the advantage that the method is easy to control. Alternatively, the steps may be repeated until the noise level in the noise-suppressed correlation is below a threshold or until the noise level in the noise suppressed correlation is not further reduced significantly. Such an alternative has the advantage that the calculation time is minimized while at the same time an optimal suppression of the correlation noise is ensured.

Advantageously, the steps of the method are repeated in cycles. During each cycle, the ion beam is preferably modulated with the ion gate being controlled by a different modulation function from a set of modulation functions for generating a different modulated ion beam. Furthermore, the correlation which is calculated during each cycle is advantageously added to a total correlation in order to obtain the mobility of the ions. This has the advantage that by choosing a set of different modulation functions, noise and systematic errors in the measured signal can me averaged out in the ion mobility spectra.

As a variant, it is possible to repeat the steps of the method in cycles while the ion gate is controlled by the same modulation function. This has the advantage that the statistics of the signal and thus of the ion mobility spectra is improved.

Alternatively, the steps of the method may be executed once only. This has the advantage that the measurement time is shorter.

If the steps of the method are repeated in cycles, it is advantageous to perform a preliminary step before repeating the cycles. In this preliminary step, the set of modulation functions is preferably selected such that for each modulation function, the false features in the correlation are located at different positions of the correlation and thus the false features are averaged out in the total correlation. For example, if the modulation function is a pseudorandom sequence and the modulation function is generated by a linear feedback shift register, a tap set of the linear feedback shift register may be chosen such that a height of the false features is minimal. Subsequently, this linear feedback shift register may be employed to generate different pseudorandom sequences by feeding it with different sets of initial values. This has the advantage that the obtained pseudorandom sequences cause false features originating from the same imperfection in the signal to be located at different positions in the correlation. Accordingly, the systematic imperfections causing false features in the ion mobility spectra can be averaged out. Furthermore, this has the advantage that if the correlation is calculated for an interval of interest, the tap set of the linear feedback shift register may be chosen such that false peaks in the correlation are located outside of the interval of interest. In that case, false peaks may be avoided in the ion mobility spectra and at the same time false features may be averaged out.

In a variant, it is possible to perform the preliminary step only once for determining one set or different sets of modulation functions. These sets of modulation function may be stored and then be employed for different measurements.

Advantageously, the correlation is calculated by calculating a circular cross correlation, an inverse Hadamard-transformation a Fourier transformation, a Laplace transformation or an M-transformation. This has the advantage that the correlation is calculated by a known formalism. Alternatively, a different formalism may be employed as well for calculating the correlation.

Preferably, the apparatus for determining the mobility of the ions includes a linear feedback shift register by which a pseudorandom sequence is generatable for the use as modulation function. This has the advantage that pseudorandom sequences are easily calculable. For example, this linear feedback shift register may be an electronic circuit or may be based on computer software. In another example, it may be included in the calculation unit.

As a variant, the apparatus may include a store for storing the modulation function. This allows for storing pseudorandom sequences that were generated by the linear feedback shift register in the store. This has the advantage that the measurement speed can be improved if the modulation function is stored in the store prior to the measurement. Additionally, the store has the advantage that it allows for storing predefined pseudorandom sequences or other modulation functions. Accordingly, the apparatus may include a store but no linear feedback shift register. In this latter case, the apparatus for determining the mobility of the ions may comprise another unit for generating the modulation function. For example, this unit may be a unit that generates predefined modulation functions or a unit that generates random sequences as modulation functions. In a variant, the apparatus may not comprise such a unit either.

Advantageously, before the correlation is calculable, a filter for enhancing the edges of the signal is applicable by the calculation unit to the signal. As a variant, the apparatus may include a separate filter unit by which a filter for enhancing the edges the signal is applicable to the signal. Both variants have the advantage that the resolution of the obtained ion mobility spectra is improved. Alternatively, it is possible that there is no filter for enhancing the edges of the signal applicable to the signal.

Preferably, the apparatus comprises a control unit by which a repetition in cycles of steps is controllable, the steps including generating the modulated ion beam with the ion gate, guiding the modulated ion beam through the drifting region, measuring the signal with the detector and calculating the correlation of the modulation function and the signal. Furthermore, the apparatus preferably comprises a summation unit by which a total correlation is calculable in order to determine the mobility of the ions, the total correlation being a sum of the correlations calculated during the cycles. Thereby, it is possible that the summation unit is a separate unit or that it is included in the calculation unit. In both cases, the control unit and the summation unit have the advantage that noise and systematic errors in the measured signal can be averaged out in the ion mobility spectra by controlling the ion gate with a different modulation function of a set of different modulation functions during each repetition of the steps.

As a variant, the apparatus may comprise the control unit and the summation unit, but the ion gate may be controllable by the same modulation function throughout all repetitions. This has the advantage that the statistics of the signal and thus of the ion mobility spectra may be improved.

Alternatively, the apparatus may not comprise such a control unit or such a summation unit.

Advantageously, the detector is a mass spectrometer. This has the advantage that for the same ions being measured a mobility spectrum and a mass spectrum may be obtained. Alternatively, if no ion mass spectrum is required, the detector may be a detector which only detects ions and does not measure an ion mass spectrum. The latter case has the advantage that the apparatus is simpler and can be constructed cheaper.

In case the detector is a mass spectrometer, the detector is preferably a time-of-flight mass spectrometer. This is advantageous because a time-of-flight mass spectrometer can optimally be combined with the ion mobility spectrometer because a time-of-flight mass spectrometer allows for measuring a large range of ion masses with a high scan rate. In a variant, the detector is a quadrupole mass spectrometer. This is advantageous if a small range of ion masses is to be determined, where a high scan rate of the quadrupole mass spectrometer may be obtained. In a further variant, the detector is an ion trap mass spectrometer. Alternatively, the detector is a different type of mass spectrometer.

In case the correlation function is a binary function or a sequence and the detector is a mass spectrometer, the mass spectrometer preferably allows for determining ion mass spectra with a repetition rate that corresponds to the bit length of the correlation function. This has the advantage that the scan rate of the mass spectrometer is adapted to the ion mobility spectrometer.

In an advantageous variant, if the detector is a mass spectrometer, the mass spectrometer preferably allows for determining ion mass spectra with a repetition rate that corresponds to a time resolution of the obtainable ion mobility spectra or to a fraction thereof. This has the advantage that the scan rate of the mass spectrometer is optimally adapted to the ion mobility spectrometer.

The above described invention may be employed as well in the fields of single and tandem liquid and gas chromatography, when a time-of-flight mass spectrometer is used as a detector. In these devices, the retention time of a substance on a column is measured. This is conceptually and functionally equivalent to the ion drift time in an ion mobility spectrometer. Usually, in order to obtain this measurement, the sample is injected onto the column as at a known time, and elutes as a single peak after the substance-specific retention time. When employing the invention in such devices, the injection of the sample onto the column is modulated in time with a modulation function that has an autocorrelation which is a two-valued function. The time dependent signal of the sample after the column is measured. Subsequently, the correlation of this signal and the modulation function is calculated. Of course, all other features that are described above for the case of a method and an apparatus for determining the ion mobility may be employed as well.

Other advantageous embodiments and combinations of features come out from the detailed description below and the totality of the claims.

BRIEF DESCRIPTION OF THE ACCOMPANYING DRAWINGS

The drawings used to explain the embodiments show:

In the figures, the same components are given the same reference symbols.

DETAILED DESCRIPTION OF THE PREFERRED EMBODIMENTS

Figure 1A:
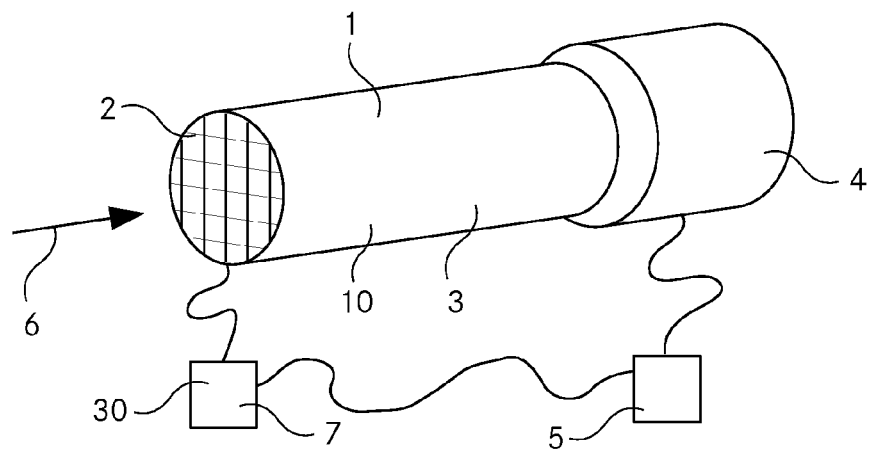
FIG. 1a is a schematic view of an apparatus according to the invention.
Figure 1B:
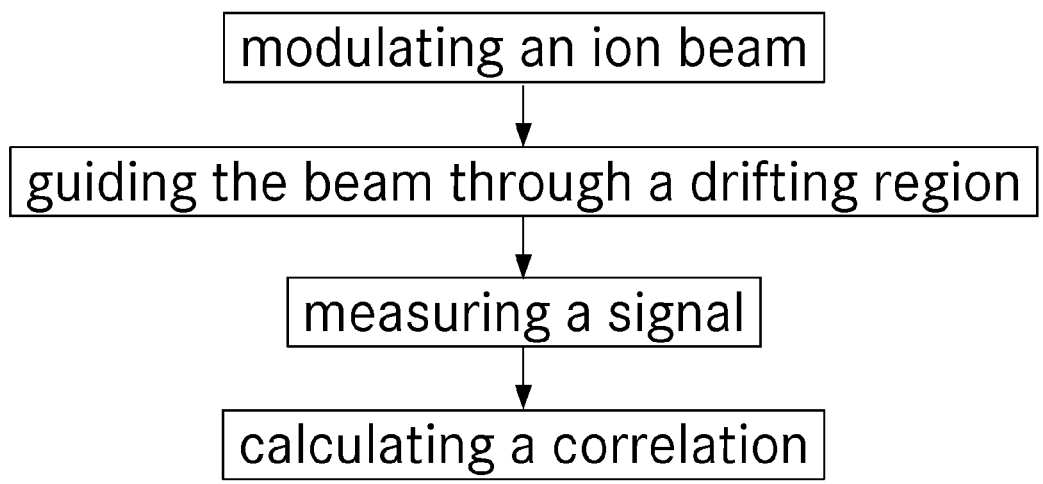
FIG. 1b is a block diagram showing the steps of the method according to the invention, respectively.

FIG. 1a shows a schematic view of an ion mobility spectrometer 1 according to the invention. This ion mobility spectrometer 1 may be used to execute a method according to the invention in order to determine the mobility of ions. FIG. 1b shows a block diagram of this method, illustrating the individual steps of the method.

The ion mobility spectrometer 1 comprises an ion gate 2, a drifting region 3, a detector 4 and a calculation unit 5. The drifting region 3 is confined by a tube 10. The ion gate 2 is arranged on an opposite end of the tube 10 than the detector 4. The ion gate 2 is of a known type. It comprises a grid of wires. If a voltage with opposite signs is applied to neighboring wires of the grid, ions of an ion beam 6 are prevented of entering the tube 10. If there is no voltage applied to the wires of the grid, the ions of the ion beam 6 may enter the tube 10. The switching of the ion gate 2 is controlled by a controller 7. The ion gate 2 may be switched between an open state, where ions may pass the ion gate 2 and a closed state, where ions are prevented of passing the ion gate 2. Those ions of the ion beam 6 that pass the ion gate 2 enter the tube 10 and drift through the drifting region 3 to the detector 4 which generates an ion signal. This ion signal is then passed to the calculation unit 5 for further processing.

When performing a measurement, the ion gate 2 is controlled by the controller 7 to switch according to a modulation function. This modulation function is a binary function that may be represented as a sequence of bits having a value "1" or "0". A value "1" corresponds to the open state of the ion gate 2, while a "0" corresponds to the closed state of the ion gate 2. The modulation function is chosen such that its autocorrelation is a two-valued function that has a peak at zero and otherwise a constant value. The ion beam 6 approaches the ion gate 2 as a continuous ion beam. When entering the tube 10, it is modulated by the ion gate 2 to yield a modulated ion beam. In flight direction of the ions, this modulated ion beam has a shape that corresponds to the modulation function. The ions of the modulated ion beam are guided through the drifting region 3 and reach the detector 4, where a signal is generated. This signal is passed to the calculation unit 5, where a correlation of the signal and the modulation function is calculated. This correlation corresponds to the ion mobility spectrum.

Figure 2:
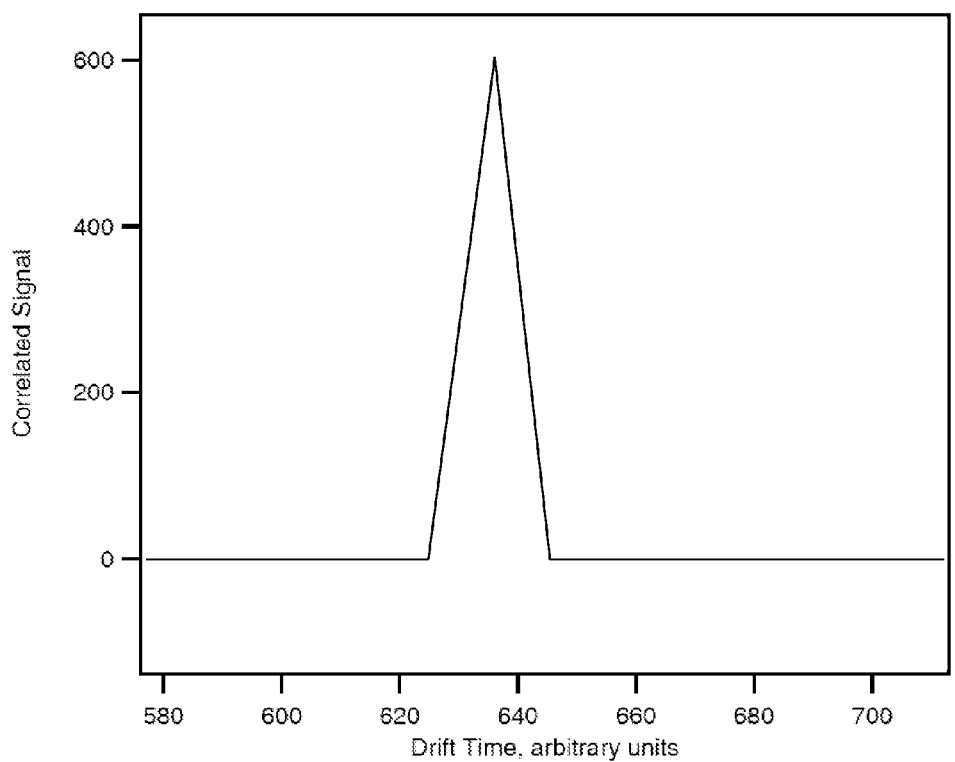
FIG. 2 illustrates a correlation of a modulation function and an idealized signal from a single species of ions.

As the autocorrelation of the modulation function is a two-valued function, the calculation of the correlation of the signal and the modulation function does not introduce additional features into the ion mobility spectrum. If, for example, the ion beam 6 comprises one single species of ions, all ions take the same time for passing the drifting region 3. Accordingly, in an ideal measurement, where the modulated ion beam has exactly the shape of the modulated function, the calculated correlation is a two-valued function like the autocorrelation of the modulation function. But in contrast to the autocorrelation, in the calculated correlation the peak position indicates the ions' time of flight (see FIG. 2).

Figure 3:
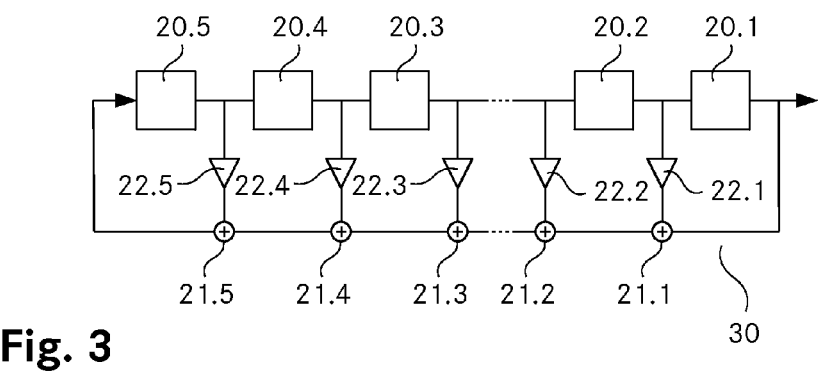
FIG. 3 is a schematic view of a linear feedback shift register that may be used to generate a pseudorandom sequence for a modulation function.

As mentioned above, the modulation function is a binary function. More precisely, it is a pseudorandom sequence of bits. It is generated by a linear feedback shift register (LFSR) 30 which is incorporated in the controller 7. FIG. 3 shows a schematic representation of this LFSR 30. In the described embodiment, the LFSR 30 is a Fibonacci implementation of an LFSR provided by a separate physical electronic circuitry.

Alternatively, it may be a Galois implementation. In a variant, it may be provided by some software that is running on a computer instead of being provided by a separate physical electronic circuitry. In other embodiments of the ion mobility spectrometer 1 an LFSR 30 may be employed as well, but the modulation function generated by the LFSR 30 could for example be a GMW sequence, a Welch-Gong transformation sequence, a Quadratic residue sequence, a Sextic residue sequence, a Twin prime sequence, a Kasami power function sequence, a Hyperoval sequence or a sequence derived from 3 or 5 maximum length sequences. In the latter case for example, the sequence may be obtained by adding up the content of corresponding bits of the 3 or 5 maximum length sequences. In that case, the addition of two 1s or of two 0s may results in a 0, while the addition of a 0 and a 1 or of a 1 and a 0 may result in a 1 (bitwise NAND). In order to achieve this addition, the controller 7 may include an addition unit which is arranged after the LFSR 30.

Alternatively, the ion mobility spectrometer 1 shown in FIG. 1a may comprise a store for storing a predefined modulation function. In that case, the modulation function may be generated by the LFSR 30 and stored in the store. When required, the modulation function may be retrieved from the store. In a variant, the ion mobility spectrometer may only comprise a store for storing a predefined modulation function and not comprise the LFSR 30. Then, the modulation function may be generated by a separate LFSR like the one shown in FIG. 3. Subsequently, the modulation function may be permanently stored in the store of the ion mobility spectrometer 1 as a predefined modulation function. For a measurement, this predefined modulation function may be retrieved from the store.

In a variant, another means than the above described LFSR 30 could be employed for generating the modulation function. In such an embodiment, the same types of modulation function could be used and the modulation function could be stored as described above.

As shown in FIG. 3, the LFSR 30 has a number of bits 20.1, . . . 20.5 which are connected in series. Furthermore, the bits 20.1, . . . 20.5 are connected by connections 22.1, . . . 22.5 with XOR-functions 21.1, . . . 21.5 that are themselves connected in series. The connections 22.1, . . . 22.5 can be individually switched on or off. Accordingly, different connection patterns between the bits 20.1, . . . 20.5 of the LFSR 30 and the XOR-functions 21.1, . . . 21.5 can be achieved by switching on or off the connections 22.1, . . . 22.5. Each such connection pattern is called a tap set of the LFSR. For generating a pseudorandom sequence, a particular tap set is chosen and the bits 20.1, . . . 20.5 of the LFSR 30 are set to a set of initial values. Subsequently, based on the values of the bits 20.1, . . . 20.5 and based on the tap set, a bit-value is generated by the XOR-functions 21.1, . . . 21.5. This bit-value is fed to a first bit 20.5 of the LFSR 30, while the values of the other bits 20.1, . . . 20.4 of the LFSR 30 are shifted by one bit towards the end of the LFSR 30. The last bit 20.1 of the LFSR 30 represents a bit of the pseudorandom sequence. By repeating the generation of a bit-value from the current values of the bits 20.1, . . . 20.5 and the tap set and by feeding the generated bit-value to the LFSR 30, the pseudorandom sequence is generated.

In the described embodiment, the pseudorandom sequence generated by the LFSR 30 is a sequence of maximum length. Accordingly, it has a length of $2^m-1$ bits, where m is the number of bits of the LFSR 30. For example, if m=7, the following tap sets are possible for obtaining a sequence of maximum length:

tap set$_{m=7}$ 1: [7, 6]
tap set$_{m=7}$ 2: [7, 4]
tap set$_{m=7}$ 3: [7, 6, 5, 4]
tap set$_{m=7}$ 4: [7, 6, 5, 2]
tap set$_{m=7}$ 5: [7, 6, 4, 2]
tap set$_{m=7}$ 6: [7, 6, 4, 1]
tap set$_{m=7}$ 7: [7, 5, 4, 3]
tap set$_{m=7}$ 8: [7, 6, 5, 4, 3, 2]
tap set$_{m=7}$ 9: [7, 6, 5, 4, 2, 1]

The numbers in these tap sets identify the open connections 22.1, . . . 22.5 of the bits 20.1, . . . 20.5 with the XOR-functions 21.1, . . . 21.5. In the given example, where m=7, the number 7 identifies the connection to the first bit 20.5 where the generated bit-value is fed to (arrow), while the number 1 identifies the connection of the second last bit 20.2 with the XOR-function 21.1. As shown in FIG. 3, the output of the LSFR 30 is always connected to the XOR-function 21.1 while the generated bit-value is always fed to the first bit 20.5.

For generating a sequence, a set of initial values is chosen and the bits 20.1, . . . 20.5 of the LFSR 30 are set accordingly. In this document, the sets of initial values are denoted in the form of a decimal number. In order to set the bits 20.1, . . . 20.5 of the LFSR 30, this number is to be represented in the form of a binary number.

In order to increase the resolution of the ion mobility spectrometer, the signal can be filtered with a filter for enhancing the edges before the correlation between the modulation function and the signal is calculated. The ion mobility spectrometer 1 shown in FIG. 1a may therefore comprise a filter. This filter may be an n-element finite difference filter, an edge enhancement filter or a filter using a different type of sharpening algorithm. It may be incorporated in the calculation unit 5 or may be a separate unit that is located between the detector 4 and the calculation unit 5.

Figure 4:
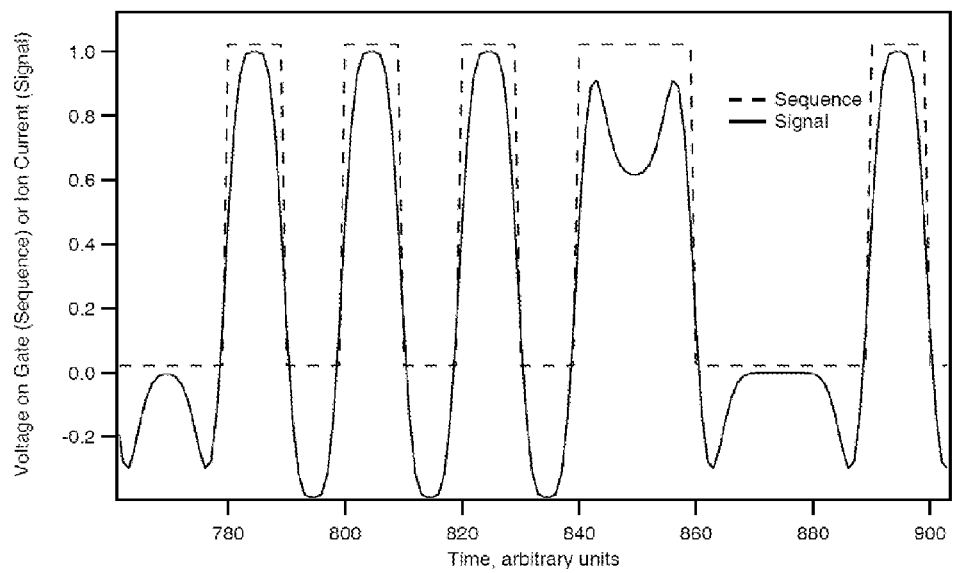
FIG. 4 illustrates a sequence of maximum length and a corresponding idealized, filtered signal with enhanced edges that is expected for an idealized signal of one ion species.
Figure 5:
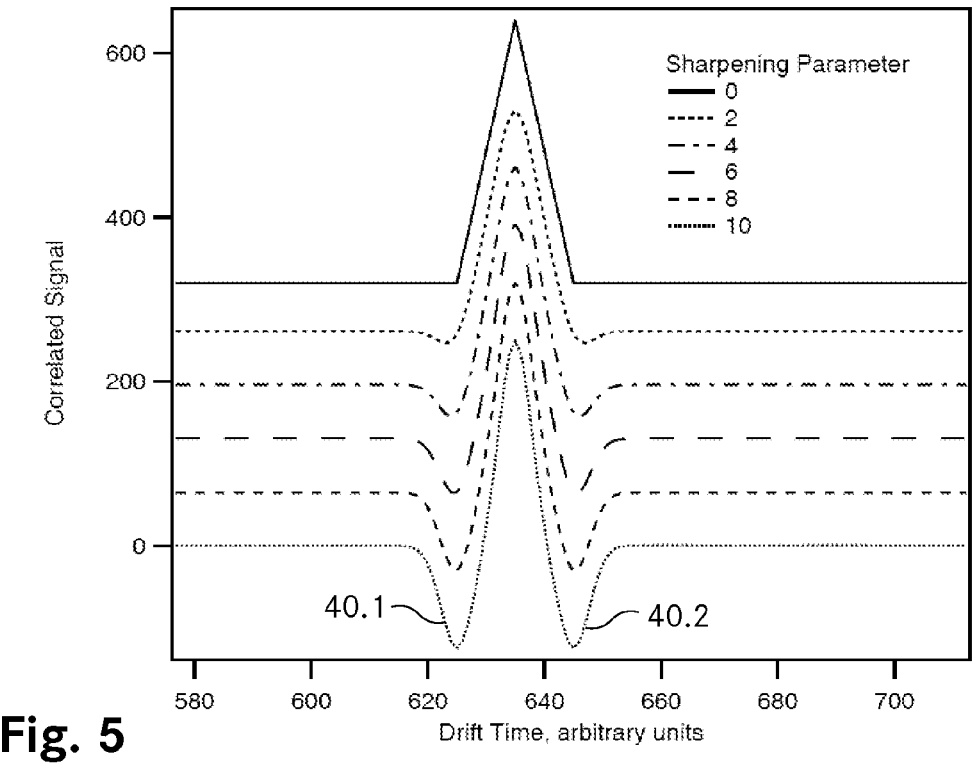
FIG. 5 illustrates correlations of a modulation function and an idealized signal from a single species of ions, wherein for the different correlations the signal is sharpened with a different sharpening parameter.
Figure 6:
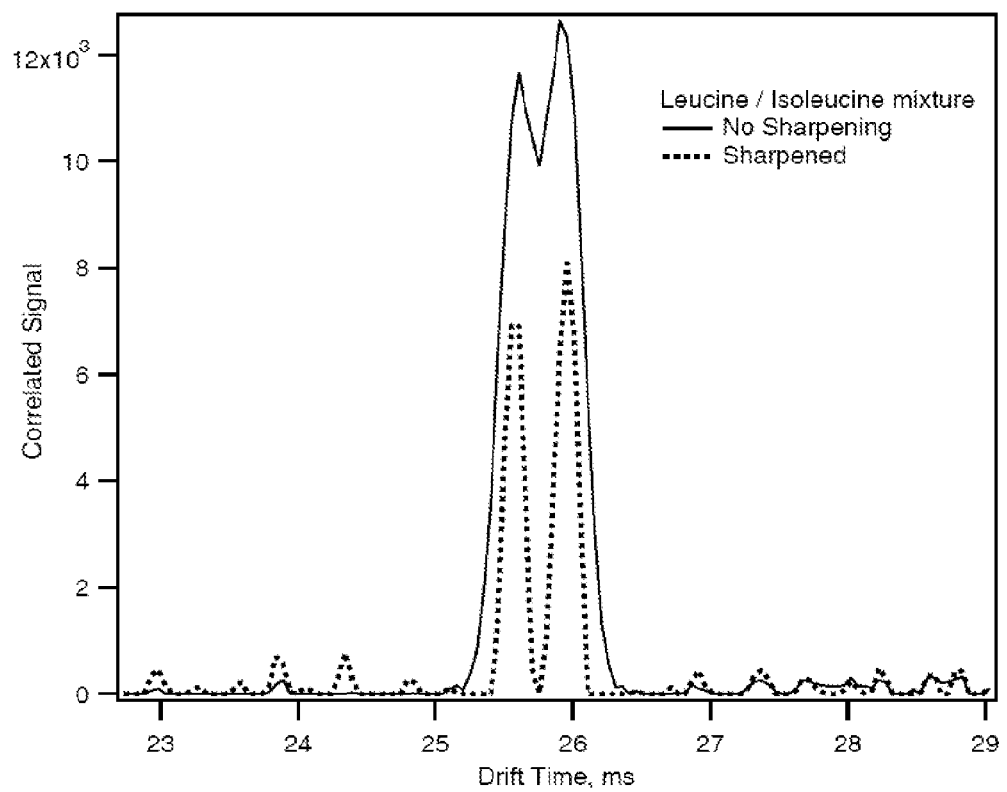
FIG. 6 is a comparison of two correlations calculated for a measurement of a Leucine/Isoleucine-mixture, once based on a filtered signal and once based on a non-filtered signal.

FIGS. 4, 5 and 6 illustrate the behavior of the filter on the example of an n-element finite difference filter. FIG. 4 shows a sequence of maximum length (dashed line) that is generated by the LFSR 30 shown in FIG. 3 having a length of m=7. The continuous line shows a filtered signal that is expected for a perfect measurement of one ion species being modulated with the shown sequence of maximum length. In reality, the ions would reach the detector 4 with a delay that corresponds to the ion drift times. Here in FIG. 4, the filtered signal is shifted in time to correspond to the sequence of maximum length in order to enable a comparison between the filtered signal and the sequence of maximum length.

Since in the ion mobility spectrometer 1 the signal is measured in bins having a specific width in time, the n-element finite difference filter comprises an algorithm of the form $$F_i = 2nD_i - \sum_{j=i+1}^{i+n} D_j - \sum_{j=i-n}^{i-1} D_j,$$

where n is a measure for the width of the filter, $D_i$ is the size of the signal's $i^{th}$ bin and $F_i$ is the filter-value's $i^{th}$ bin. In order to obtain the filtered signal, each filter-value $F_i$ is added to the corresponding bin $D_i$ of the measured signal. When doing so, the filter-values $F_i$ and the signal $D_i$ are multiplied with a weight factor before adding the filter-values to the signal. These weight factors are based on n, the width of the filter, with $0<=n<=n_{max}$:

$$D_i^{Filtered} = \frac{1-n}{n_{max}} D_i + \frac{n}{n_{max}} F_i.$$

FIG. 5 shows calculated correlations of the modulation function and the signal shown in FIG. 4 with the signal being filtered with different sharpening parameters n. The peak indicating the time of flight of the ions becomes sharper with increasing sharpening parameter n. But at the same time, there is an overshoot 40.1, 40.2 on both sides of the peak which becomes stronger with increasing sharpening parameter n. Therefore, the filtering has the effect that peaks originating from ions having a similar time of flight may be resolved better. This is illustrated in FIG. 6 on the example of an ion mobility spectrum for a Leucine/Isoleucine-mixture, where the peaks that represent the time of flight of Leucine and Isoleucine, respectively, can be resolved better if the signal is filtered.

Instead of increasing the resolution of the ion mobility spectrometer 1 by filtering the signal with a filter for enhancing the edges before the correlation between the modulation function and the signal is calculated, the resolution of the ion mobility spectrometer 1 may be increased by calculating from the signal a blurred signal and by calculating a difference between the signal and the blurred signal by subtracting the blurred signal from the signal, and by subsequently calculating the correlation of the modulation function and the difference between the signal and the blurred signal. In order to enable these calculations, the calculation unit 5 of the ion mobility spectrometer 1 shown in FIG. 1a provides the required functionality. In a variant hereto, the ion mobility spectrometer 1 may comprise a special calculation unit which provides the required functionality. In this variant, the special calculation unit is arranged between the detector and the calculation unit 5. Furthermore, in order to enable this way of increasing the resolution of the ion mobility spectrometer, the detector 4 of the ion mobility spectrometer 1 measures the signal of the modulated ion beam with a time resolution that is ten times better than the width in time of the modulation function's bits. In a variant, the time resolution provided by the detector may be three to ten or even more times better than the modulation function's bits' width.

Figure 7A:
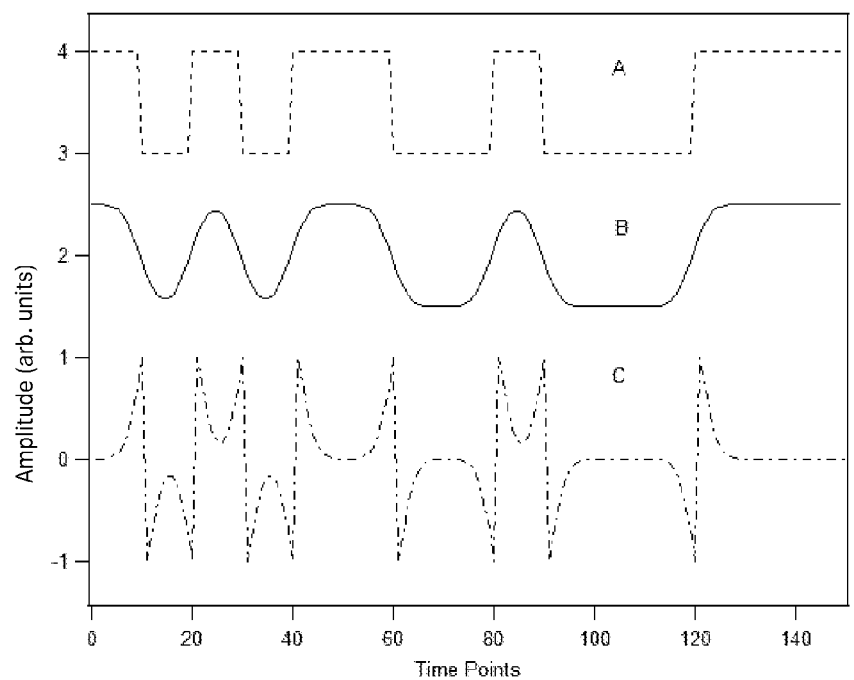
FIG. 7a is a comparison of an unprocessed signal, a blurred signal and a difference between the signal and the blurred signal.
Figure 7B:
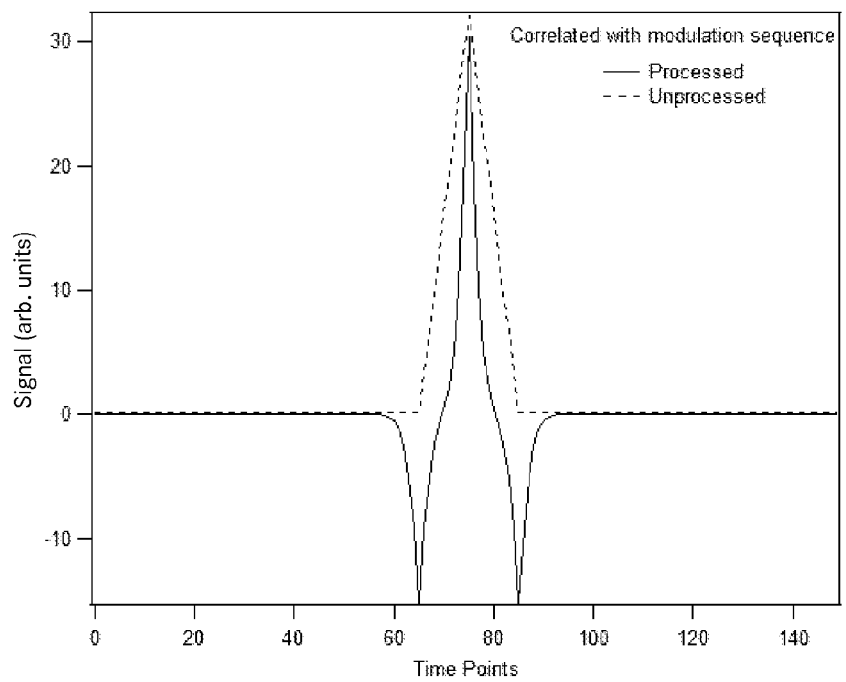
FIG. 7b is a comparison of two correlations calculated from a modulation function and the unprocessed signal and the difference, respectively.

FIGS. 7a and 7b illustrate the alternative method for increasing the resolution of the ion mobility spectrometer 1. For this purpose, FIG. 7a shows an unprocessed signal A of one single ion species, a blurred signal B and a difference C between the signal A and the blurred signal B. The signal A is ten times oversampled as compared to the modulation function's bit width. The blurred signal B is the signal A convoluted with a Gaussian having a full width at half maximum which is 1.5 the width in time of a modulation function's bit, while the difference C is the subtraction of the blurred signal B from the signal A. Therefore, the difference C can be considered as a processed signal.

FIG. 7b shows the correlation of the modulation function with the unprocessed signal A and compares it with the correlation of the modulation function with the difference C. As one can see, the correlation of the modulation function with the difference C provides a sharper peak than the correlation of the modulation function with the unprocessed signal A. At the same time, the correlation of the modulation function with the difference C provides negative values on both sides of the peak which do not carry real information. Accordingly, these negative values may be set to zero or any other arbitrary value.

Figure 8:
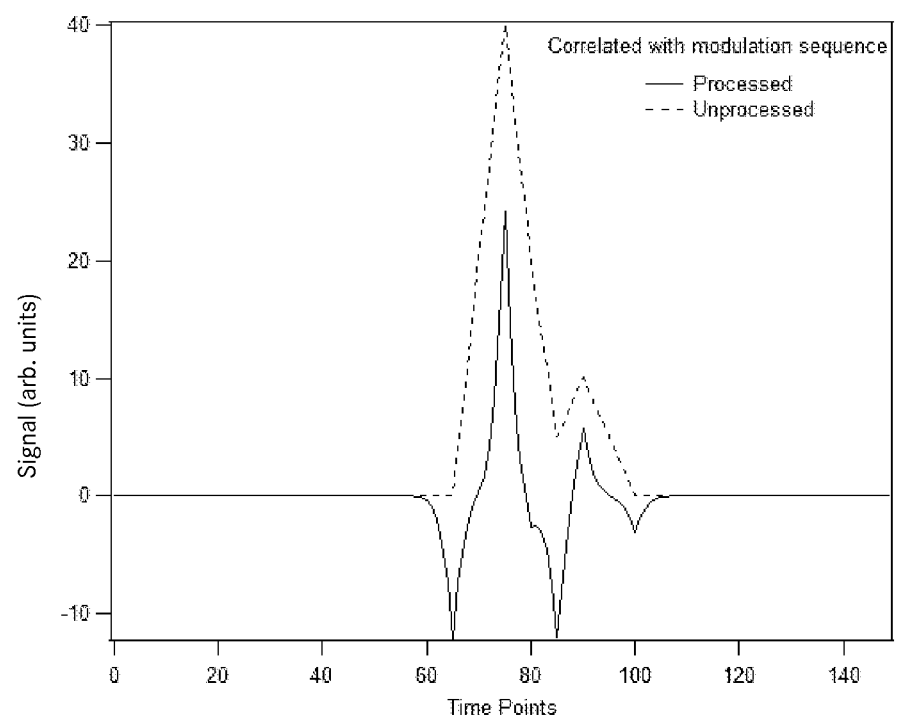
FIG. 8 is a further comparison of two correlations calculated from a modulation function and an unprocessed signal and a difference, respectively, wherein the signal carries a signature of two different ion species having a similar ion mobility.

Similar to FIG. 7b, FIG. 8 shows the correlation of the modulation function with an unprocessed signal and compares it with the correlation of the modulation function with the difference between the unprocessed signal and a blurred signal. In contrast to FIG. 7b, the signal used for calculating the correlations shown in FIG. 8 comprises a signature of two different ion species having a similar ion mobility. In this example too, the peaks of the correlation of the modulation function with the difference are sharper than the peaks of the correlation of the modulation function with the unprocessed signal. Also, both peaks in the correlation of the modulation function with the difference have negative values on both their sides. Despite these negative values, the relative intensities of the two peaks are the same in both correlations shown in FIG. 8. Accordingly, the negative values on the sides of the peaks do not have any negative effect if there are two ion signatures to be resolved which are close to each other. Therefore, these negative values can be set to zero or any other arbitrary value.

Since this method for increasing the resolution of the ion mobility spectrometer worsens the signal to noise ratio in the correlation as a pay-off for the increased resolution, the method is less useful if the statistical noise in the signal has a notably amplitude as compared to the ion signatures to be resolved in the signal. Nonetheless, the method's usefulness can be increased for obtaining a better signal to noise ratio in the correlation by blurring the blurred signal more. For this reason, the Gaussian used for the convolution with the signal may be chosen broader. But the full width at half maximum of the Gaussian should not become much larger than the width in time of a bit of the modulation function because otherwise, the ion signatures to be resolved get washed out. Ideally, the Gaussian's full width at half maximum is of the order of the width in time of one bit of the modulation function. As an alternative way for obtaining a better signal to noise ratio in the correlation, the blurred signal may be weighted less than the unprocessed signal when calculating the difference. For example, the integral intensity of the blurred signal may be weighted 90% or 80% of the integral intensity of the unprocessed signal. But if there are ion signatures to be resolved in a signal which comprises comparably high statistical noise, the integral intensity of the blurred signal may even be weighted less than 80% of the integral intensity of the unprocessed signal. With weighting the blurred signal less, the impact of the method for increasing the resolution of the ion mobility spectrometer is reduced until at a weight of 0% of the blurred signal's integral intensity, the method has no effect on the correlation anymore. Accordingly, weighting the blurred signal less than the unprocessed signal is more effective for optimizing the amount of sharpening relative to the signal to noise ratio. Therefore, the method is most effective if a Gaussian with a full width at half maximum of the order of the width in time of one bit of the modulation function is used for calculating the blurred signal and if the sharpening is tuned by weighting the blurred signal in order to obtain for each measurement an acceptable signal to noise ratio.

In order to improve the signal to noise ratio in the correlation and in the obtained ion mobility spectra, an additional denoising routine is provided by the calculation unit 5 of the ion mobility spectrometer 1. Alternatively, this denoising routine may be provided by a further calculation unit which is arranged after the calculation unit 5 or the ion mobility spectrometer 1 may not provide such a denoising routine at all. If the ion mobility spectrometer 1 provides the denoising routine, the routine is employable independent on whether the ion mobility spectrometer 1 provides a filter as illustrated in FIGS. 4 to 6 or an alternative method for increasing the resolution as illustrated in FIGS. 7a, 7b and 8 and on whether this filter or this alternative method is employed or not.

The denoising routine allows for suppressing so-called correlation noise in the correlation. This correlation noise originates from statistical noise in the measured signal which is calculated into the correlation when calculating the correlation. In a first step of the routine, a noise level of the correlation noise is determined by analyzing a region in the correlation where no signature of ions is located. Since the ion mobility spectrometer 1 performs time-of-flight measurements, the used region is located in the first part of the correlation where no ion has reached the detector yet. Accordingly, the maximum size of the region is limited by the mobility of the fastest ions and depends on the length of the ion's flight path which corresponds to the drifting region 3. The region must be shorter than the time which is needed by the fastest ions for passing the drifting region 3. Here in the ion mobility spectrometer 1, the region is determined when the ion mobility spectrometer 1 is built. With this, only ions with a drifting speed less than a maximum speed should be measured. Alternatively, in a variant of the ion mobility spectrometer 1, the region may be determined before each measurement in order to adapt the routine to different samples comprising fastest ions with different drifting speeds. In either variant, once the region is known and the correlation is calculated, a first value of the noise level is determined by calculating the mean value of the correlation in the region. Furthermore, a second value of the noise level is determined by calculating the standard deviation of the correlation in the same region. In a second step of the routine, a noise-suppressed correlation is calculated from the correlation. In this step, the function $$f(x) = \begin{cases} 0, & \text{for } x < \mu - \sigma \\ x \cdot \left(\frac{(x-\mu)}{2\sigma} + 0.5\right), & \text{for } \mu - \sigma \le x < \mu + \sigma \\ x, & \text{for } \mu + \sigma \le x \end{cases}$$

with μ as the first value of the noise level and σ as the second value of the noise level is applied to each value of the correlation in order to obtain the noise-suppressed correlation. Consequently, in this noise-suppressed correlation, values which are very likely to be correlation noise are reduced to amount zero, whereas values which are very likely to be an ion signature are maintained, while values which are probably correlation noise are reduced depending on their probability of being correlation noise.

In a variant of this second step of the routine, the noise-suppressed correlation may be calculated differently. For example, each value of the correlation may be tested for its position on a cumulative distribution function of a Gaussian probability distribution with the first value of the noise level as mean value and with the second value of the noise level as standard deviation. Subsequently, the value of the correlation may be multiplied by the cumulative distribution function's value at this position. Alternatively, a scaling factor may be calculated based on the value of the cumulative distribution at the position of the correlation's value by dividing the distribution's value by 5 and by subsequently adding 0.8. Then, the scaling factor may be multiplied with the correlation's value for obtaining the respective value of a noise-suppressed correlation. Consequently, in this noise-suppressed correlation, values which are likely to be correlation noise are reduced to amount something more than 80 of the respective value of the originally calculated correlation, while values which are less likely to be correlation noise are nearly kept maintained as compared to the originally calculated correlation.

Figure 9:
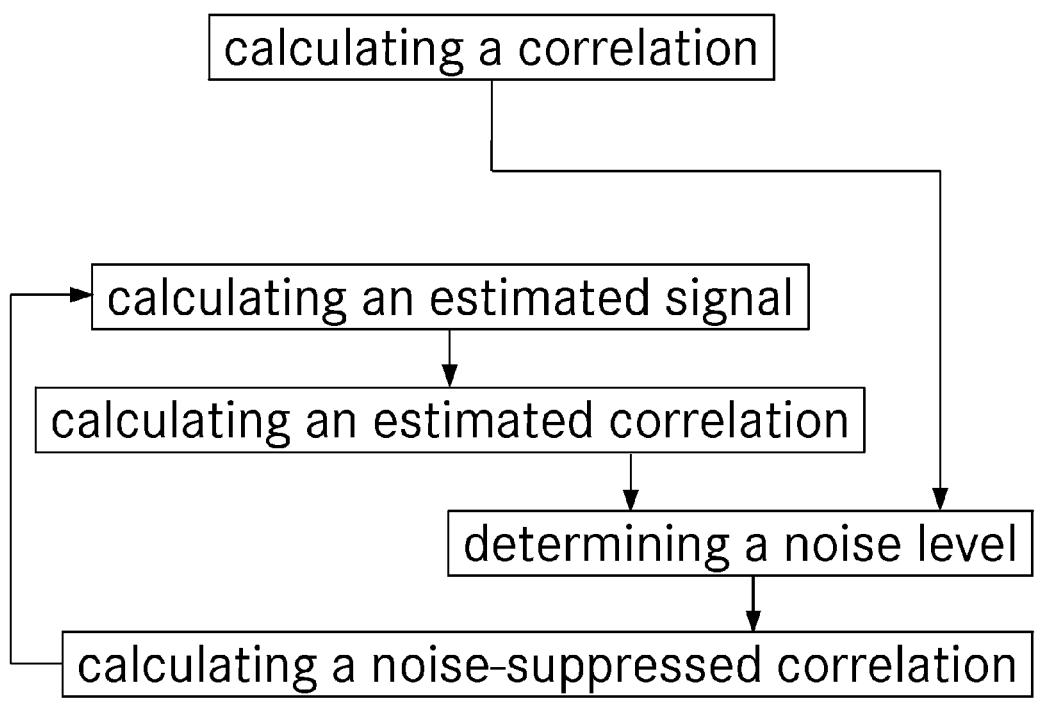
FIG. 9 is a block diagram of a denoising routine and a repetition function for repeatedly applying the denoising routine.

In addition to the two steps of the denoising routine described above, the calculation unit 5 or the additional calculation unit, respectively, provides a repetition function for repeating the denoising routine. The steps of the denoising routine and the repetition function are illustrated in FIG. 9. As shown, the noise-suppressed correlation is convoluted with the modulation function for obtaining an estimated signal and subsequently, the estimated signal is correlated with the modulation function for obtaining an estimated correlation. With this estimated correlation, an improved correlation is provided for being fed to the denoising routine. Accordingly, the two steps of the denoising routine are applied to the estimated correlation for obtaining an improved noise-suppressed correlation. This improved noise-suppressed correlation may either be used as the ion mobility spectrum or the steps for obtaining a further estimated signal and estimated correlation and the steps of the denoising routine may be repeated again.

Figure 10:
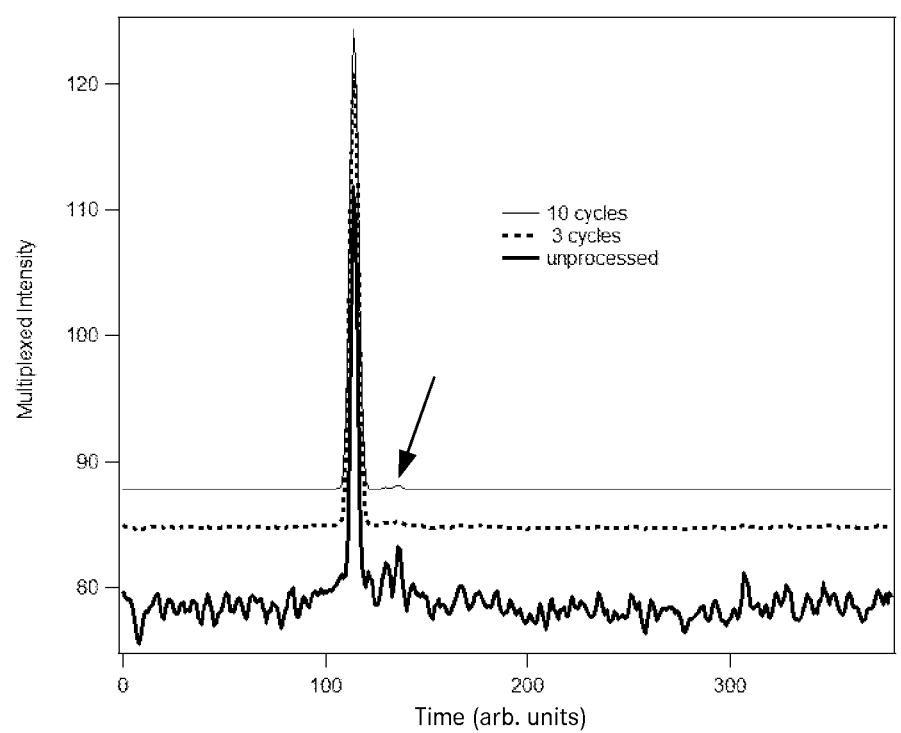
FIG. 10 illustrates a correlation calculated from a measurement being compared to a correlation after applying the denoising routine three times and a correlation after applying the denoising routine ten times, respectively.

In the ion mobility spectrometer 1 as shown in FIG. 1*a*, the denoising routine is executed ten times in total. The effect of these repetitions is illustrated in FIG. 10, where the correlation of a measured signal with the modulation function is compared with the noise-suppressed correlation after three repetitions of the denoising routine and after ten repetitions of the denoising routine. As indicated by the arrow, a signature of ions having a smaller ion mobility is recovered besides the main ion peak.

In an alternative embodiment, the denoising routine may be executed a different, fixed number of times or may be repeated until the noise-suppressed correlation does not change significantly as compared to the correlation based on which said noise-suppressed correlation has been calculated.

Figure 11A:
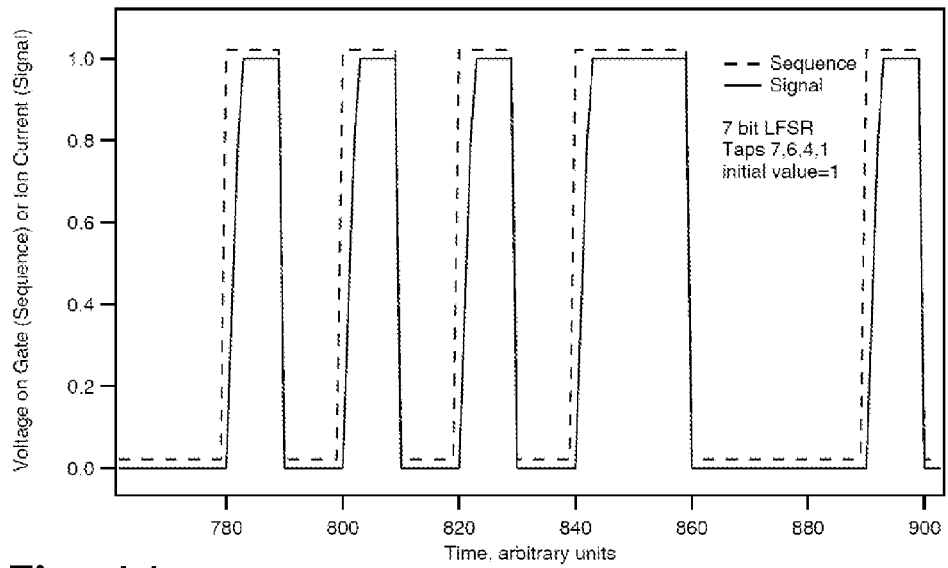
FIGS. 11A, 11B, 11C and 11D illustrate four different systematic deviations of the modulated ion beam from an ideal shape.
Figure 11B:
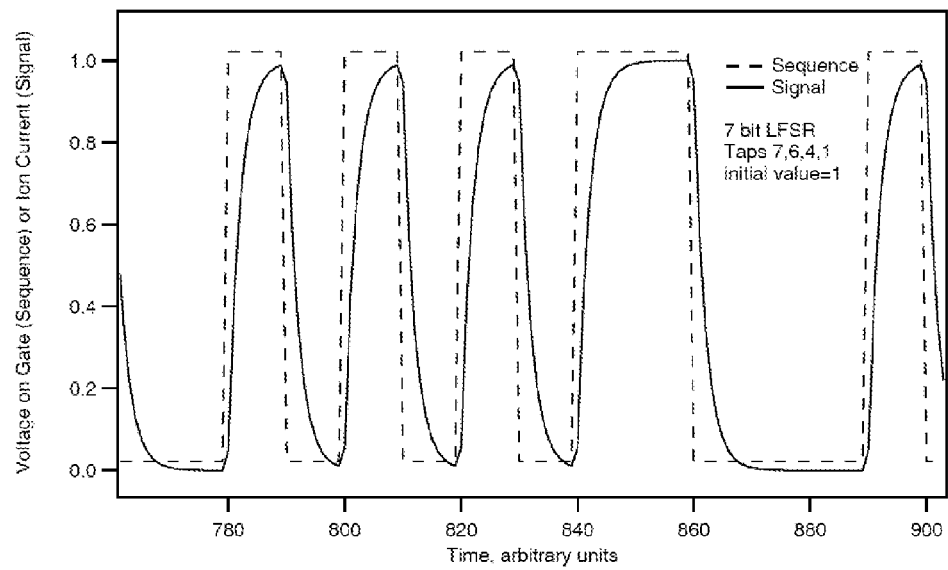
Figure 11C:
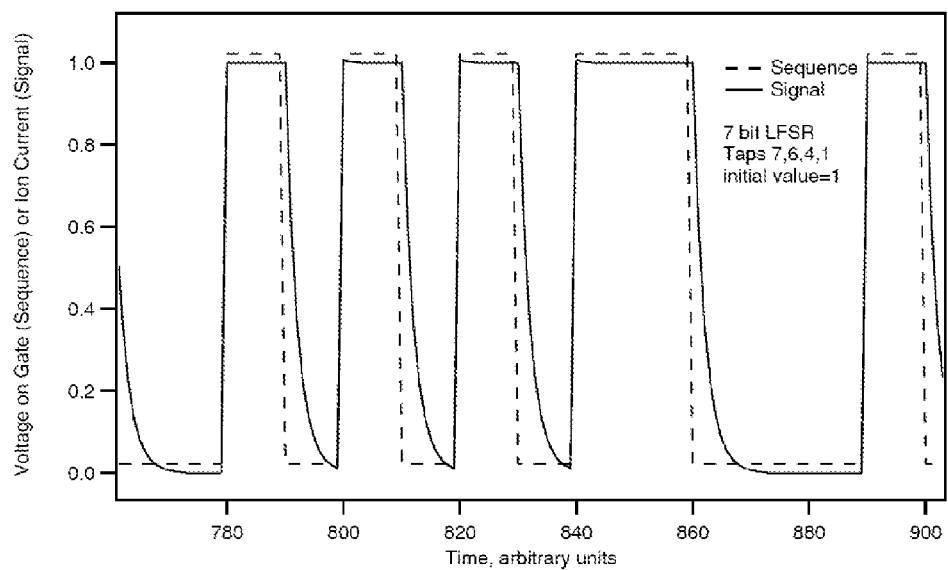
Figure 11D:
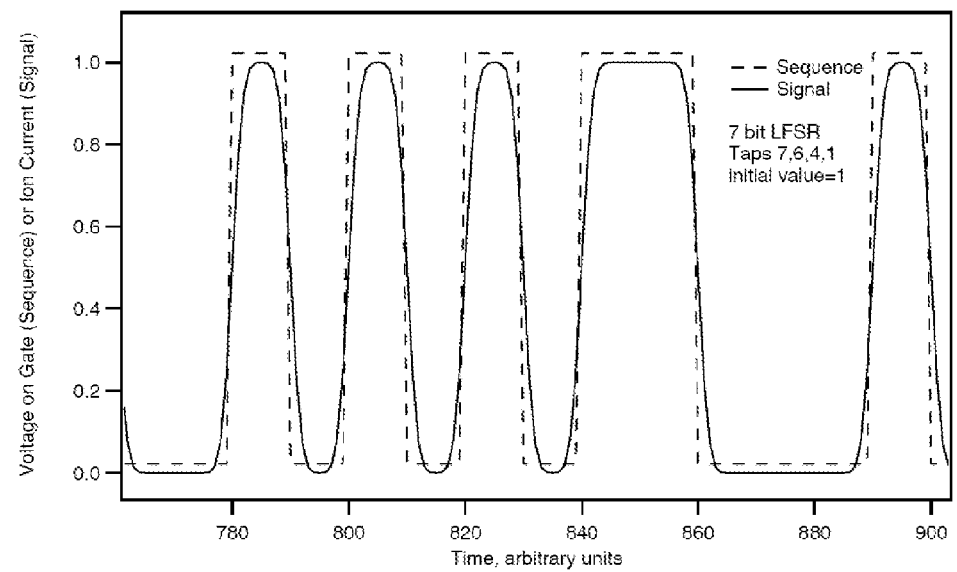

In a real measurement, the modulated ion beam has never the perfect shape of the modulation function. There will always be some systematic deviations from the perfect shape. Four types of such deviations are illustrated in FIGS. 11*a*, 11*b*, 11*c* and 11*d*. In FIG. 11*a*, a deviation is shown which is caused by depletion. In this case, when the ion gate is switched into the open state, it takes some time before ions start to enter the drifting region. Accordingly, the modulation function's bits in the modulated ion beam get a slope towards lower times of flight. As another possible systematic deviation, FIG. 11*b* shows a modulated ion beam that is distorted by a delayed response of the ions. This may occur due to a non-uniform gas flow in the drifting region or due to other reasons. It distorts the modulation function's bits in the modulated ion beam in a manner similar to a rectangular signal being distorted by an RC filter. A further type of deviation is a tailing of the ions. As shown in FIG. 11 *c*, in this case, some ions get delayed when passing the drifting region. Therefore, the modulation function's bits in the modulated ion beam obtain a tail towards higher times of flight. A fourth type of systematic deviations is caused by diffusion of the ions. FIG. 11*d* illustrates how in that case the edges of the modulation function's bits in the modulated ion beam become diffused during the ions' passage through the drifting region.

Figure 12:
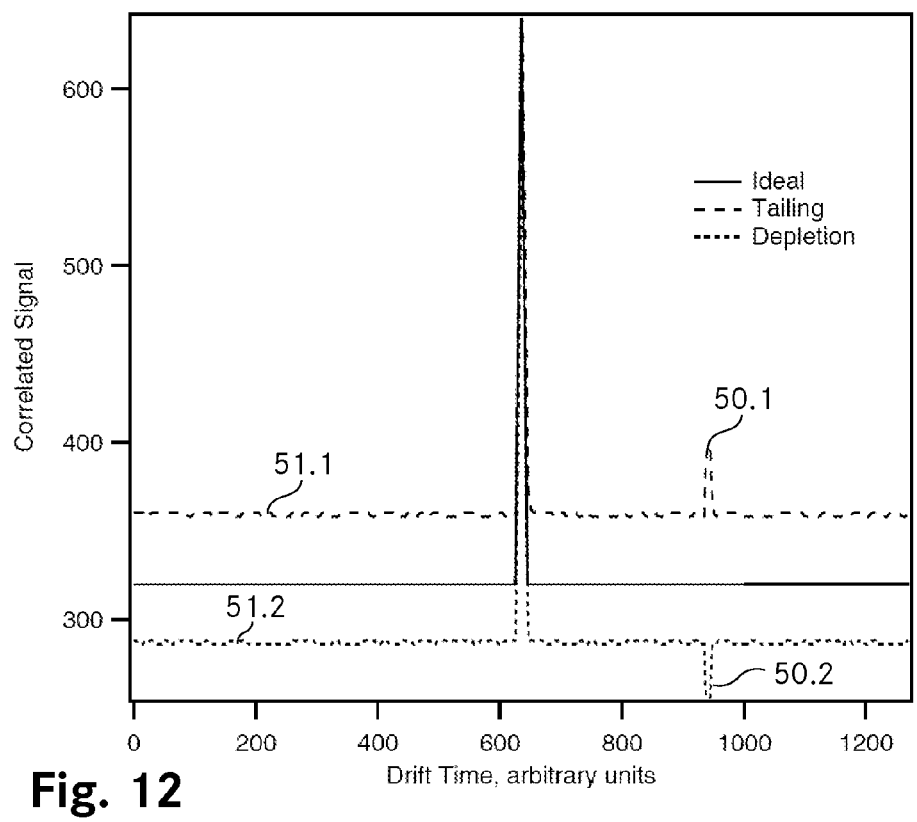
FIG. 12 illustrates simulated correlations illustrating that tailing and depletion of ions may cause a false peak in the correlation which is not originating from a particular species of ions.

From the four types of systematic deviations, the diffusion is the only one which is symmetric in time. Accordingly, it causes only a broadening of the peaks in the calculated correlation. This broadening may be at least partially taken into account for by filtering the signal before calculating the correlation. The other three types of systematic deviations may as well cause a broadening of the peaks which may be taken into account for by filtering the signal and thus sharpening the correlation. But additionally, due to their asymmetry in time, they cause a shifting of the peak positions and may cause features at other positions of the correlation. For example, as shown in FIG. 12, tailing and depletion may cause a false peak 50.1, 50.2 in the correlation that is not originating from a particular species of ion. Additionally, both these deviations may cause false features 51.1, 51.2 in the baseline of the correlation. In order to take into account for the shifting of the peaks, the false peaks 50.1, 50.2 and the false features 51.1, 51.2, there are different approaches to be chosen. The shifting for example may be taken into account for by calibrating the ion mobility spectrometer accordingly.

Figure 13:
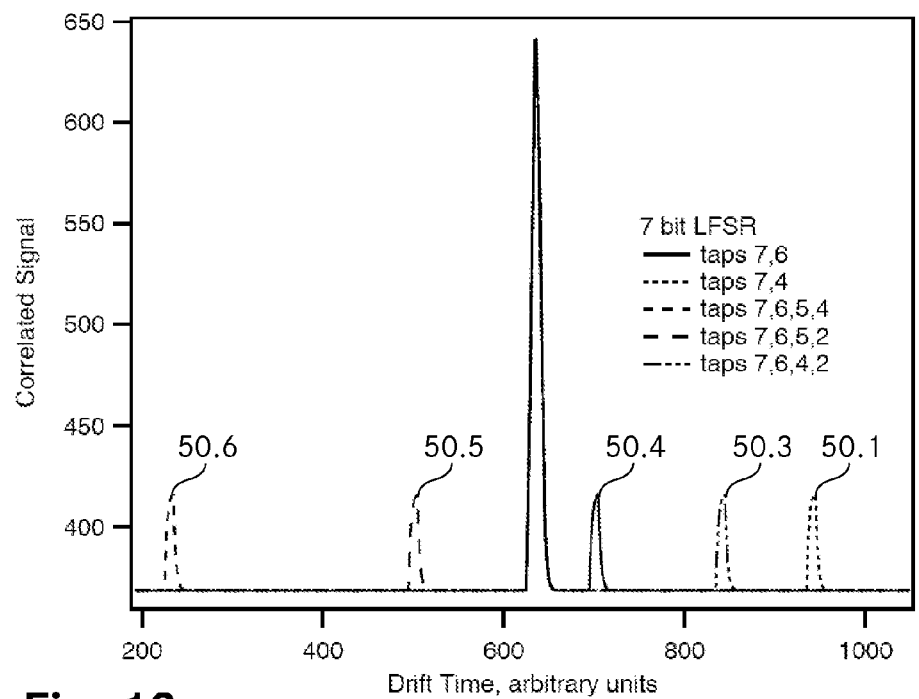
FIG. 13 illustrates simulated correlations illustrating that the position of false peaks in the correlation may be shifted by using a different tap set for the linear feedback shift register.

FIG. 13 illustrates an approach for how to deal with a false peak 50.1, 50.3, . . . 50.6. It shows simulated correlations that are calculated by assuming a measurement of a single species of ions, wherein some of the ions are tailing. These simulated correlations are based on modulation functions that are pseudorandom sequences of maximum length. The sequences are generated by an LFSR 30 as shown in FIG. 3. The LSFR 30 has a length of 7 bits. The difference between the simulated correlations is that for each correlation, a different tap set of the LFSR 30 is used for generating the pseudorandom sequences of maximum length. As shown, the position of the false peak 50.1, 50.3, . . . 50.6 depends on the tap set of the LFSR 30. Since the position does not depend on the set of initial values used for generating the pseudorandom sequences of maximum length, it is sufficient to choose a tap set such that the false peak 50.1, 50.3, . . . 50.6 is located outside of an interval of interest. In FIG. 13, if the interval of interest is for example between a drift time of 400 and 800 arbitrary units, the tap sets [7, 4], [7, 6, 4, 2] or [7, 6, 5, 4] may be used because the position of the false peak 50.1, 50.3, 50.6 is then located outside of the interval of interest.

Figure 14:
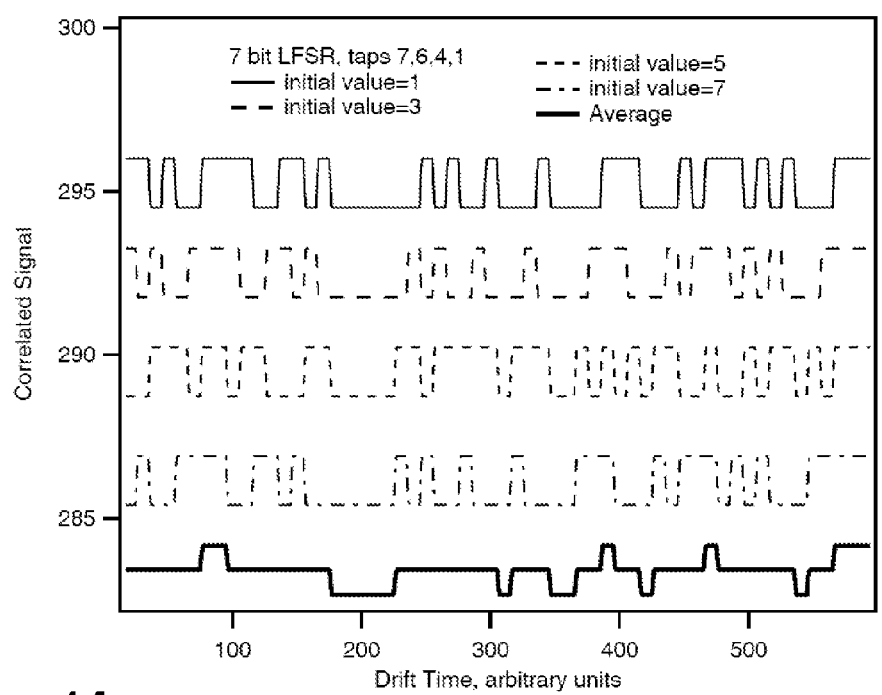
FIG. 14 illustrates four different modulation functions that are generated with the same linear feedback shift register and the same tap set but with different sets of initial values.

One approach for how to deal with false features 51.1, 51.2 like the ones shown in FIG. 12 is to choose a tap set of the LFSR 30 such that the false features 51.1, 51.2 have a minimal height. Another approach which may additionally be employed is illustrated in FIG. 14, where four different modulation functions are shown. All four modulation functions are pseudorandom sequences of maximum length that have been generated with the LFSR 30 as shown in FIG. 3. The LFSR 30 has had a length of 7 bits and the tap set [7, 6, 4, 1] has been used. For each of the four modulation functions shown in FIG. 14, a different set of initial values has been used. As a consequence, the average of the obtained modulation functions provides fewer steps than the individual modulation functions. This effect can be used in the method for obtaining an ion mobility spectrum. When doing so, a measurement is repeated in cycles by using for each cycle a different modulation function that is generated by using a different set of initial values. Subsequently, the obtained correlations are added to a total correlation. Since for each modulation function, false features 51.1, 51.2 like the ones shown in FIG. 12 are located at different positions of the baseline of the calculated correlation, the false features 51.1, 51.2 get averaged out.

In order to implement this averaging option into an ion mobility spectrometer, the latter may comprise a summation unit for calculating the total correlation from the correlations obtained from the measurements with different modulation functions. This summation unit may be incorporated into the calculation unit 5 (see FIG. 1*a*) or it may be a separate unit arranged after the calculation unit 5.

Figure 15:
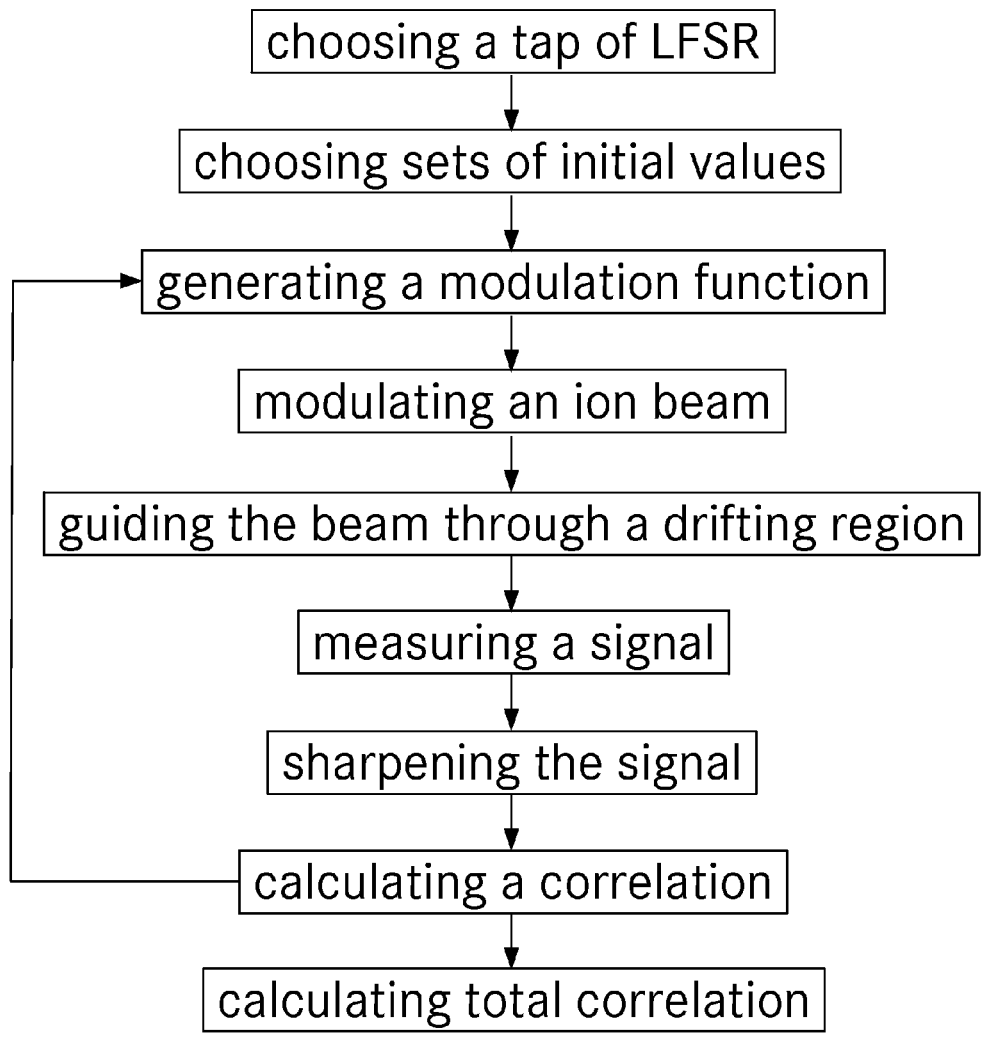
FIG. 15 is a block diagram of a method that considers several possible optimization options.

When considering these optimization options, the method according to the invention which is shown in FIG. 1*b* may be extended. FIG. 15 shows a scheme of a method that considers these options. The individual steps of the method are illustrated.

In this extended method, an LFSR is used for generating the modulation function. Accordingly, the tap set of the LFSR is chosen first. This choice is based on the criterions that any false peak caused by tailing or depletion of the ions is located outside of the interval of interest of the correlation and that false features caused by tailing, depletion or a delayed response of the ions have a low intensity in the correlation. In a second step, different sets of initial values of the LFSR are chosen. These sets are chosen such that false features caused by tailing, depletion or a delayed response of the ions are located at different positions in the correlation. Since the false peaks and the false features depend on systematic deviations of the modulated ion beam from a prefect shape, they may be simulated according to the characteristics of the ion mobility spectrometer that is used. Accordingly, the choice of the tap set of the LFSR and of the sets of initial values may be based on such simulations.

Once the tap set of the LFSR and the sets of initial values are chosen, some steps of the method are repeated in cycles. During each cycle, a modulation function is generated first. This modulation function is based on the preliminary chosen tap set and on one of the preliminary chosen sets of initial values. During each cycle, the set of initial values is different. Once the modulation function is generated, the ion beam is modulated by the ion gate according to the modulation function. The modulated ion beam is then guided through the drifting region and a signal of the ions is measured after the ions have passed the drifting region. Subsequently, the measured signal is sharpened with a filter or the above described alternative method for sharpening the signal and the correlation of the modulation function and the sharpened signal is calculated. Subsequently, the denoising routine is applied to the correlation in order to suppress the correlation noise in the correlation. Thereafter, the noise-suppressed correlation is convoluted with the modulation function and correlated with the modulation function in order to obtain an estimated correlation on which the denoising routine is applied again. After having repeated this convolution and correlation with the modulation function and the denoising routine ten times in total, a final, noise-suppressed correlation is obtained as result of the particular cycle. In each cycle, this final, noise-suppressed correlation is either stored in a separate store or fed directly to a summation unit for adding the correlations calculated during the cycles. If during each cycle, the correlation is stored in a separate store, the correlations may be fed to the summation unit after the last cycle is executed. Finally, all correlations obtained during the cycles are added by the summation unit. The resulting total correlation corresponds to the ion mobility spectrum.

In this extended method, the step of generating the modulation functions may be executed before the measurements are repeated in cycles. In that case, the modulation functions are stored in a store before repeating the measurement in cycles. Subsequently, during each cycle, a different modulation function is retrieved from the store.

In a further embodiment of the above described ion mobility spectrometer, the detector is a mass spectrometer. This enables to obtain an ion mobility spectrum and a mass spectrum of the same ions. The mass spectrometer employed may be a time-of-flight mass spectrometer, a quadrupole mass spectrometer, an ion trap mass spectrometer or another type of mass spectrometer. In order to optimise the performance of the ion mobility spectrometer and the mass spectrometer, the mass spectrometer is capable of obtaining mass spectra with a high repetition rate. In particular, it may be permanently operatable with this high repetition rate or it may be operatable with this high repetition rate for at least the time interval that is required for measuring one ion mobility spectrum by using the entire modulation function. For example, the modulation function of the ion mobility spectrometer may comprise bits with a length of about 250 µm. In this case, the mass spectrometer may repeatedly obtain a mass spectrum within 250 µm or within a fraction of 250 µm. The latter case is particularly advantageous, if the time-resolution of the obtained ion mobility spectra is better than 250 µm. For example, if the ion mobility spectra have a time-resolution of 50 µm caused by diffusion of the ions in the drifting region, the mass spectrometer may obtain mass spectra with a repetition rate of 50 µm or a fraction thereof. Of course, these particular bit length, time-resolution and repetition rates are only examples for illustration purposes. They may be adapted to the particular requirements of the measurements to be performed.

In summary, it is to be noted a method and an apparatus are provided that allow for determining an ion mobility with a higher signal to noise ratio while providing the same measurement speed as known from the prior art.

While the system, apparatus, process and method herein described constitute preferred embodiments of this invention, it is to be understood that the invention is not limited to this precise system, apparatus, process and method, and that changes may be made therein without departing from the scope of the invention which is defined in the appended claims.

What is claimed is:

1. A method for determining a mobility of ions, including the steps of:
   modulating an ion beam with an ion gate which is controlled by a modulation function for generating a modulated ion beam, wherein said modulation function is a pseudorandom sequence generated with a linear feedback shift register and wherein an autocorrelation of said modulation function is a two-valued function,
   guiding said modulated ion beam through a drifting region,
   measuring a signal of said modulated ion beam after said modulated ion beam has passed said drifting region,
   calculating a correlation of said modulation function and said signal in order to determine said mobility of said ions,
   wherein an interval of interest of possible ion drift times is chosen from said correlation and in that the method comprises a step of selecting said modulation function by selecting a tap set of said linear feedback shift register such that as many as possible false peaks in said correlation are located outside of said interval of interest.

2. The method according to claim 1, wherein said modulation function is a maximum length sequence, a GMW sequence, a Welch-Gong transformation sequence, a Quadratic residue sequence, a Sextic residue sequence, a Twin prime sequence, a Kasami power function sequence, a Hyperoval sequence or a sequence derived from 3 or 5 maximum length sequences.

3. The method according to claim 1, wherein a step of enhancing edges of said signal with a filter by filtering said signal before calculating said correlation.

4. The method according to claim 3, wherein said filter is an n-element finite difference filter, edge enhancement filter, or a filter using a different type of sharpening algorithm.

5. The method according to claim 1, wherein by a step of calculating from the signal a blurred signal and a step of calculating a difference between the signal and the blurred signal by subtracting the blurred signal from the signal, before the correlation of the modulation function and the difference between the signal and the blurred signal is calculated.

6. The method according claim 1, wherein a step of selecting said modulation function by selecting a set of initial values for feeding to said linear feedback shift register such that false features in said correlation have a low height.

7. The method according to claim 1, wherein a step of determining a noise level of a correlation noise in a region of the calculated correlation where no signal of measured ions is expected and a step of calculating a noise-suppressed correlation by suppressing the correlation noise in the correlation, both steps being executed after the step of calculating the correlation.

8. The method according to claim 1, wherein:
   repeating said steps in cycles, wherein during each cycle, said ion beam is modulated with said ion gate being controlled by a different modulation function from a set of modulation functions for generating a different modulated ion beam, and in
   adding said correlation which is calculated during each said cycle to a total correlation in order to determine said mobility of said ions.

9. The method according to claim 8, wherein performing a preliminary step before repeating said cycles, wherein said set of modulation functions is selected such that for each modulation function, false features in said correlation are located at different positions of said correlation and thus said false features are averaged out in said total correlation.

10. The method according to claim 1, wherein said correlation is calculated by calculating a circular cross correlation, an inverse Hadamard-transformation a Fourier transformation, a Laplace transformation or an M-transformation.

11. An apparatus for determining a mobility of ions, including:
    an ion gate which is controlled by a modulation function for generating from an ion beam a modulated ion beam;
    a drifting region through which said modulated ion beam is guidable;
    a detector by which a signal of said modulated ion beam is measurable after said modulated ion beam has passed said drifting region;
    calculation unit by which a correlation of said modulation function and said signal is calculable in order to determine said mobility of said ions; and
    a linear feedback shift register by which a pseudorandom sequence is generatable for the use as said modulation function, wherein an autocorrelation of said modulation function is a two-valued function,
    wherein said linear feedback shift register comprises a tap set selected such that as many as possible false peaks in said correlation are located outside of an interval of interest of possible ion drift times chosen from said correlation.

12. The apparatus according to claim 11, wherein before said correlation is calculable, a filter for enhancing edges of said signal is applicable by said calculation unit to said signal.

13. The apparatus according to claim 11, wherein:
    a control unit by which a repetition in cycles of steps is controllable, said steps including generating said modulated ion beam with said ion gate, guiding said modulated ion beam through said drifting region, measuring said signal with said detector and calculating said correlation of said modulation function and said signal; and
    a summation unit by which a total correlation is calculable in order to determine said mobility of said ions, said total correlation being a sum of said correlations calculated during said cycles.

14. The apparatus according to claim 11, wherein said detector is a mass spectrometer.

15. The apparatus according to claim 14 wherein said mass spectrometer is a time-of-flight masss spectrometer.

16. The apparatus according to claim 14, wherein said mass spectrometer allows for determining ion mass spectra with a repetition rate that corresponds to a time resolution of the obtainable ion mobility spectra or to a fraction thereof.

* * * * *